United States Patent
Mueller et al.

(10) Patent No.: US 9,241,739 B2
(45) Date of Patent: Jan. 26, 2016

(54) SPINAL STABILIZING AND GUIDING FIXATION SYSTEM

(75) Inventors: Marcel Mueller, Therwil (CH); Meret Labhart, Aarau (CH)

(73) Assignee: DePuy Synthes Products, Inc., Raynham, MA (US)

( * ) Notice: Subject to any disclaimer, the term of this patent is extended or adjusted under 35 U.S.C. 154(b) by 251 days.

(21) Appl. No.: 13/063,323

(22) PCT Filed: Sep. 11, 2009

(86) PCT No.: PCT/US2009/056692
§ 371 (c)(1),
(2), (4) Date: Jun. 1, 2011

(87) PCT Pub. No.: WO2010/030906
PCT Pub. Date: Mar. 18, 2010

(65) Prior Publication Data
US 2011/0270314 A1    Nov. 3, 2011

Related U.S. Application Data

(60) Provisional application No. 61/096,453, filed on Sep. 12, 2008.

(51) Int. Cl.
    *A61B 17/70*    (2006.01)
(52) U.S. Cl.
    CPC ............ *A61B 17/7046* (2013.01); *A61B 17/704* (2013.01); *A61B 17/705* (2013.01); *A61B 17/7053* (2013.01); *A61B 17/7041* (2013.01)
(58) Field of Classification Search
    USPC ................... 606/246–279; 403/391, 396, 399; 174/40 CC, 68.1, 72 A, 88 R
    See application file for complete search history.

(56) References Cited

U.S. PATENT DOCUMENTS

| 802,896 A | 10/1905 | Webb |
| 2,338,659 A * | 1/1944 | Morehouse ................. 248/74.3 |

(Continued)

FOREIGN PATENT DOCUMENTS

| DE | 4329220 A1 | 9/1995 |
| DE | 20207785 U1 | 9/2003 |

(Continued)

OTHER PUBLICATIONS

International Patent Application No. PCT/US2009/056692: International Search Report and Written Opinion dated Dec. 3, 2009, 14 pages.

(Continued)

*Primary Examiner* — Jan Christopher Merene
*Assistant Examiner* — Steven Cotroneo
(74) *Attorney, Agent, or Firm* — Baker & Hostetler LLP

(57) ABSTRACT

A system to stabilize and guide the growth of the spinal column includes an elongated support member having a width and a length and a guiding connector having a bone connecting portion and a guiding portion. The bone connecting portion secures the guiding connector to a vertebrae and the guiding portion has a bearing element with a passageway adapted to receive the elongated support member. The bearing element permits relative sliding movement of the elongated support element in the passageway of the bearing element. The system may further include a bone fixation element has an elongated support member receiving channel, a locking mechanism and a bone anchoring portion. The bone anchoring portion secures the bone fixation element to bone. The locking mechanism secures the elongated support member in the channel. The guiding connector is moveable along the elongated support member to permit and control the growth of the spinal column along a predetermined path.

13 Claims, 18 Drawing Sheets

(56) References Cited

U.S. PATENT DOCUMENTS

| | | | |
|---|---|---|---|
| 2,396,925 A * | 3/1946 | Morehouse | 248/68.1 |
| 3,173,987 A * | 3/1965 | Potruch | 174/545 |
| 3,463,427 A | 8/1969 | Fisher | |
| 4,447,934 A | 5/1984 | Anscher | |
| 4,719,905 A | 1/1988 | Steffee | |
| 4,805,602 A | 2/1989 | Puno et al. | |
| 4,944,475 A | 7/1990 | Ono et al. | |
| 4,946,458 A | 8/1990 | Harms et al. | |
| 5,207,678 A * | 5/1993 | Harms et al. | 606/267 |
| 5,242,446 A * | 9/1993 | Steffee et al. | 606/254 |
| 5,282,825 A | 2/1994 | Muck et al. | |
| 5,304,178 A * | 4/1994 | Stahurski | 606/263 |
| 5,312,410 A | 5/1994 | Miller et al. | |
| 5,383,882 A | 1/1995 | Buess et al. | |
| 5,395,374 A | 3/1995 | Miller et al. | |
| 5,413,576 A | 5/1995 | Rivard | |
| 5,417,684 A | 5/1995 | Jackson et al. | |
| 5,449,361 A | 9/1995 | Preissman | |
| 5,474,555 A | 12/1995 | Puno et al. | |
| 5,486,174 A | 1/1996 | Fournet-Fayard et al. | |
| 5,501,684 A | 3/1996 | Schlapfer et al. | |
| 5,534,001 A | 7/1996 | Schlapfer et al. | |
| 5,536,270 A | 7/1996 | Songer et al. | |
| 5,540,698 A | 7/1996 | Preissman et al. | |
| 5,549,608 A | 8/1996 | Errico et al. | |
| 5,562,661 A | 10/1996 | Yoshimi et al. | |
| 5,575,792 A | 11/1996 | Errico et al. | |
| 5,578,033 A | 11/1996 | Errico et al. | |
| 5,584,834 A | 12/1996 | Errico et al. | |
| 5,586,984 A | 12/1996 | Errico et al. | |
| 5,601,261 A | 2/1997 | Koike | |
| 5,605,458 A | 2/1997 | Bailey et al. | |
| 5,609,593 A | 3/1997 | Errico et al. | |
| 5,609,594 A | 3/1997 | Errico et al. | |
| 5,645,544 A | 7/1997 | Tai et al. | |
| 5,669,911 A | 9/1997 | Errico et al. | |
| 5,672,175 A | 9/1997 | Martin | |
| 5,683,392 A | 11/1997 | Richelsoph et al. | |
| 5,683,404 A | 11/1997 | Johnson | |
| 5,688,273 A | 11/1997 | Errico et al. | |
| 5,690,630 A | 11/1997 | Errico et al. | |
| 5,725,582 A | 3/1998 | Bevan et al. | |
| 5,728,098 A | 3/1998 | Sherman et al. | |
| 5,733,285 A | 3/1998 | Errico et al. | |
| 5,772,663 A | 6/1998 | Whiteside et al. | |
| 5,782,831 A * | 7/1998 | Sherman et al. | 606/86 A |
| 5,797,911 A | 8/1998 | Sherman et al. | |
| 5,860,987 A | 1/1999 | Ratcliff et al. | |
| 5,863,293 A | 1/1999 | Richelsoph | |
| 5,868,748 A | 2/1999 | Burke | |
| 5,879,350 A | 3/1999 | Sherman et al. | |
| 5,885,286 A | 3/1999 | Sherman et al. | |
| 5,902,305 A | 5/1999 | Beger | |
| 5,938,663 A * | 8/1999 | Petreto | 606/278 |
| 5,964,760 A | 10/1999 | Richelsoph | |
| 6,010,503 A | 1/2000 | Richelsoph et al. | |
| 6,053,917 A | 4/2000 | Sherman et al. | |
| 6,074,391 A | 6/2000 | Metz-Stavenhagen et al. | |
| 6,077,263 A | 6/2000 | Ameil et al. | |
| 6,083,224 A * | 7/2000 | Gertzbein et al. | 606/250 |
| 6,090,110 A | 7/2000 | Metz-Stavenhagen | |
| 6,132,432 A | 10/2000 | Richelsoph | |
| 6,248,105 B1 | 6/2001 | Schlapfer et al. | |
| 6,261,287 B1 | 7/2001 | Metz-Stavenhagen | |
| 6,280,442 B1 | 8/2001 | Barker et al. | |
| 6,325,802 B1 * | 12/2001 | Frigg | 606/263 |
| 6,355,040 B1 | 3/2002 | Richelsoph et al. | |
| RE37,665 E | 4/2002 | Ralph et al. | |
| 6,368,321 B1 | 4/2002 | Jackson | |
| 6,402,752 B2 | 6/2002 | Schaffler-Wachter et al. | |
| 6,440,132 B1 | 8/2002 | Jackson | |
| 6,485,491 B1 | 11/2002 | Farris et al. | |
| 6,514,255 B1 | 2/2003 | Ferree | |
| 6,533,226 B2 | 3/2003 | Geiger | |
| 6,537,276 B2 | 3/2003 | Metz-Stavenhagen | |
| 6,554,831 B1 | 4/2003 | Rivard et al. | |
| 6,565,565 B1 | 5/2003 | Yuan et al. | |
| 6,585,740 B2 | 7/2003 | Schlapfer et al. | |
| 6,616,667 B1 | 9/2003 | Steiger et al. | |
| 6,641,588 B2 | 11/2003 | Citron et al. | |
| 6,660,004 B2 | 12/2003 | Barker et al. | |
| 6,689,140 B2 | 2/2004 | Cohen | |
| 6,695,852 B2 | 2/2004 | Gleason | |
| 6,716,214 B1 | 4/2004 | Jackson | |
| 6,770,075 B2 | 8/2004 | Howland | |
| 6,783,527 B2 | 8/2004 | Drewry et al. | |
| 6,802,844 B2 | 10/2004 | Ferree | |
| 6,843,791 B2 | 1/2005 | Serhan | |
| 6,869,433 B2 | 3/2005 | Glascott | |
| 6,933,440 B2 * | 8/2005 | Ichikawa et al. | 174/507 |
| 6,964,666 B2 | 11/2005 | Jackson | |
| RE39,089 E | 5/2006 | Ralph et al. | |
| 7,073,415 B2 | 7/2006 | Casutt et al. | |
| 7,125,410 B2 | 10/2006 | Freudiger | |
| 7,128,743 B2 | 10/2006 | Metz-Stavenhagen | |
| 7,131,467 B2 | 11/2006 | Gao et al. | |
| 7,163,539 B2 | 1/2007 | Abdelgany et al. | |
| 7,250,052 B2 | 7/2007 | Landry et al. | |
| 7,322,548 B2 | 1/2008 | Mielke et al. | |
| 7,338,490 B2 * | 3/2008 | Ogilvie et al. | 606/276 |
| 7,452,360 B2 | 11/2008 | Trudeau et al. | |
| 7,547,319 B2 | 6/2009 | Segal et al. | |
| 7,592,546 B2 * | 9/2009 | Johansson | 174/95 |
| 7,645,282 B2 | 1/2010 | Huxel et al. | |
| 7,708,762 B2 | 5/2010 | McCarthy et al. | |
| 7,785,352 B2 * | 8/2010 | Snyder et al. | 606/263 |
| 7,803,174 B2 | 9/2010 | Denis et al. | |
| 7,806,895 B2 | 10/2010 | Weier et al. | |
| 8,029,513 B2 | 10/2011 | Konno et al. | |
| 8,029,546 B2 | 10/2011 | Capote et al. | |
| 8,096,998 B2 | 1/2012 | Cresina | |
| 8,137,356 B2 | 3/2012 | Hestad et al. | |
| 8,172,772 B2 | 5/2012 | Zwolinski et al. | |
| 8,216,245 B2 | 7/2012 | Gil et al. | |
| 8,221,464 B2 | 7/2012 | Belliard et al. | |
| 8,231,626 B2 * | 7/2012 | Hulliger et al. | 606/74 |
| 8,246,659 B2 | 8/2012 | Vonwiller et al. | |
| 8,257,367 B2 | 9/2012 | Bryant et al. | |
| 8,323,318 B2 | 12/2012 | Baccelli et al. | |
| 8,469,960 B2 | 6/2013 | Hutton et al. | |
| 8,469,966 B2 | 6/2013 | Allen et al. | |
| 8,632,572 B2 | 1/2014 | Darst Rice et al. | |
| 8,814,910 B2 | 8/2014 | Baccelli et al. | |
| 8,870,869 B2 | 10/2014 | Meunier et al. | |
| 8,870,870 B2 | 10/2014 | Baccelli et al. | |
| 9,039,708 B2 | 5/2015 | Larroque-Lahitette | |
| 2002/0069537 A1 | 6/2002 | Wenzler | |
| 2002/0117321 A1 * | 8/2002 | Beebe et al. | 174/72 A |
| 2002/0120272 A1 | 8/2002 | Yuan et al. | |
| 2002/0138077 A1 | 9/2002 | Ferree | |
| 2003/0100896 A1 | 5/2003 | Biedermann et al. | |
| 2003/0125742 A1 | 7/2003 | Yuan et al. | |
| 2004/0111088 A1 | 6/2004 | Picetti et al. | |
| 2004/0143265 A1 | 7/2004 | Landry et al. | |
| 2004/0157186 A1 * | 8/2004 | Abels et al. | 433/10 |
| 2004/0172022 A1 | 9/2004 | Landry et al. | |
| 2004/0193160 A1 | 9/2004 | Richelsoph | |
| 2004/0199169 A1 | 10/2004 | Koons et al. | |
| 2004/0236330 A1 | 11/2004 | Purcell et al. | |
| 2004/0267264 A1 | 12/2004 | Konieczynski et al. | |
| 2005/0080420 A1 | 4/2005 | Farris et al. | |
| 2005/0143737 A1 | 6/2005 | Pafford et al. | |
| 2005/0171537 A1 | 8/2005 | Mazel et al. | |
| 2005/0177179 A1 | 8/2005 | Baynham et al. | |
| 2005/0216001 A1 | 9/2005 | David | |
| 2005/0228378 A1 | 10/2005 | Kalfas et al. | |
| 2005/0228385 A1 | 10/2005 | Iott et al. | |
| 2005/0234451 A1 | 10/2005 | Markworth | |
| 2005/0288671 A1 | 12/2005 | Yuan et al. | |
| 2006/0004357 A1 | 1/2006 | Lee et al. | |
| 2006/0052818 A1 | 3/2006 | Drake et al. | |
| 2006/0064091 A1 | 3/2006 | Ludwig et al. | |
| 2006/0084993 A1 | 4/2006 | Landry et al. | |
| 2006/0084996 A1 | 4/2006 | Metz-Stavenhagen | |

(56) References Cited

U.S. PATENT DOCUMENTS

| | | |
|---|---|---|
| 2006/0089643 A1 | 4/2006 | Mujwid |
| 2006/0111779 A1 | 5/2006 | Petersen et al. |
| 2006/0129149 A1 | 6/2006 | Iott et al. |
| 2006/0142761 A1 | 6/2006 | Landry et al. |
| 2006/0149233 A1 | 7/2006 | Richelsoph |
| 2006/0149241 A1 | 7/2006 | Richelsoph et al. |
| 2006/0229611 A1 | 10/2006 | Avery et al. |
| 2006/0241594 A1 | 10/2006 | McCarthy et al. |
| 2006/0241624 A1 | 10/2006 | Kizuka et al. |
| 2006/0247636 A1 | 11/2006 | Yuan et al. |
| 2006/0247668 A1 | 11/2006 | Park |
| 2007/0043365 A1 | 2/2007 | Ritland |
| 2007/0049932 A1 | 3/2007 | Richelsoph et al. |
| 2007/0090238 A1 | 4/2007 | Justis |
| 2007/0118121 A1 | 5/2007 | Purcell et al. |
| 2007/0123860 A1* | 5/2007 | Francis et al. ............... 606/61 |
| 2007/0123870 A1 | 5/2007 | Jeon et al. |
| 2007/0135817 A1 | 6/2007 | Ensign |
| 2007/0161987 A1 | 7/2007 | Capote et al. |
| 2007/0161994 A1* | 7/2007 | Lowery et al. ............... 606/61 |
| 2007/0250061 A1 | 10/2007 | Chin et al. |
| 2007/0270817 A1 | 11/2007 | Rezach |
| 2008/0058812 A1 | 3/2008 | Zehnder |
| 2008/0086126 A1 | 4/2008 | Miller |
| 2008/0103502 A1 | 5/2008 | Capote et al. |
| 2008/0177323 A1 | 7/2008 | Null et al. |
| 2008/0215095 A1 | 9/2008 | Biedermann et al. |
| 2008/0234743 A1 | 9/2008 | Marik |
| 2008/0262552 A1 | 10/2008 | Kim |
| 2008/0269810 A1 | 10/2008 | Zhang et al. |
| 2008/0294194 A1 | 11/2008 | Capote et al. |
| 2008/0312692 A1 | 12/2008 | Brennan et al. |
| 2009/0088803 A1 | 4/2009 | Justis et al. |
| 2009/0093847 A1 | 4/2009 | Wilcox |
| 2010/0087864 A1 | 4/2010 | Klein et al. |
| 2010/0094345 A1 | 4/2010 | Saidha et al. |
| 2010/0191286 A1 | 7/2010 | Butler |
| 2010/0276051 A1 | 11/2010 | Kanehira |
| 2010/0313428 A1 | 12/2010 | Mocanu |
| 2010/0324599 A1 | 12/2010 | Montello et al. |
| 2012/0010629 A1 | 1/2012 | Mire et al. |
| 2012/0109200 A1 | 5/2012 | Cahill et al. |
| 2012/0265249 A1 | 10/2012 | Fielding et al. |
| 2013/0012955 A1 | 1/2013 | Lin et al. |
| 2013/0012995 A1 | 1/2013 | Butterfield et al. |
| 2013/0079827 A1 | 3/2013 | Neary et al. |
| 2013/0261680 A1 | 10/2013 | Baccelli et al. |
| 2013/0268011 A1 | 10/2013 | Rezach et al. |

FOREIGN PATENT DOCUMENTS

| | | |
|---|---|---|
| EP | 408489 B1 | 1/1991 |
| EP | 612507 B1 | 12/1998 |
| EP | 683644 B1 | 6/2000 |
| EP | 1 269 929 | 1/2003 |
| EP | 0 837 656 | 12/2003 |
| EP | 1313403 B1 | 10/2006 |
| EP | 1 198 205 | 11/2006 |
| EP | 1665994 B1 | 6/2008 |
| GB | 2414674 B | 8/2009 |
| JP | 6-154258 | 6/1994 |
| JP | 2005-510286 | 4/2005 |
| WO | WO 2004/052218 | 6/2004 |
| WO | WO 2006/088452 A2 | 8/2006 |
| WO | WO 2007/045892 | 4/2007 |
| WO | WO 2008/027940 | 3/2008 |
| WO | WO 2008/146185 A1 | 12/2008 |
| WO | WO 2009/015100 | 1/2009 |
| WO | WO 2010/030906 | 3/2010 |
| WO | WO 2010/120989 | 10/2010 |
| WO | WO 2010/148231 | 12/2010 |
| WO | WO 2012/154772 A2 | 11/2012 |

OTHER PUBLICATIONS

International Patent Application No. PCT/US2010/031178: International Search Report dated Jun. 22, 2010, 8 pages.

International Patent Application No. PCT/US2010/031178: International Preliminary Report on Patentability dated Jun. 14, 2011, 21 pages.

International Patent Application No. PCT/US2010/039037: International Search Report Dated Jan. 9, 2010, 5 pages.

International Patent Application No. PCT/US2010/039037: International Preliminary Report on Patentability dated Jul. 11, 2011, 14 pages.

* cited by examiner

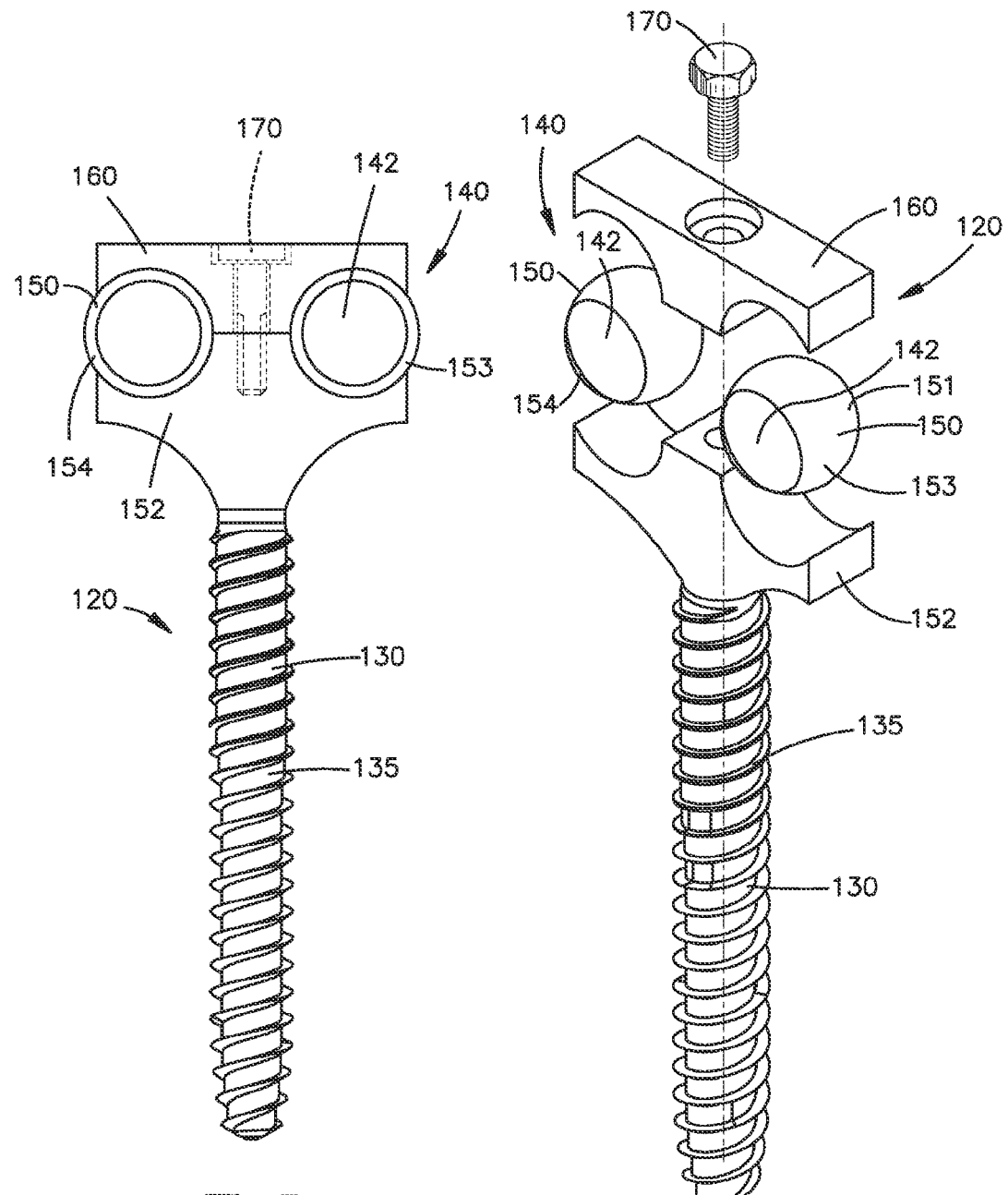

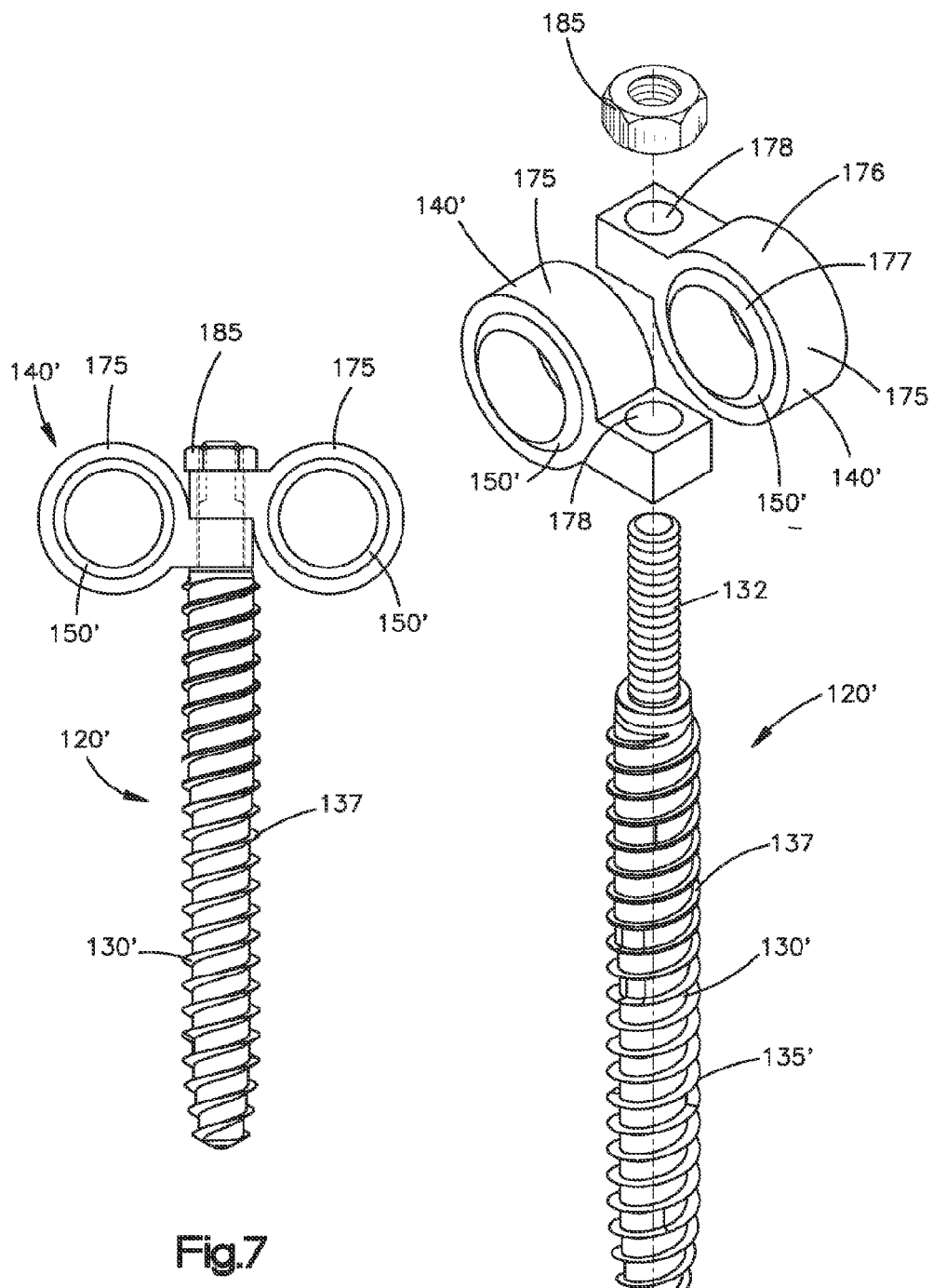

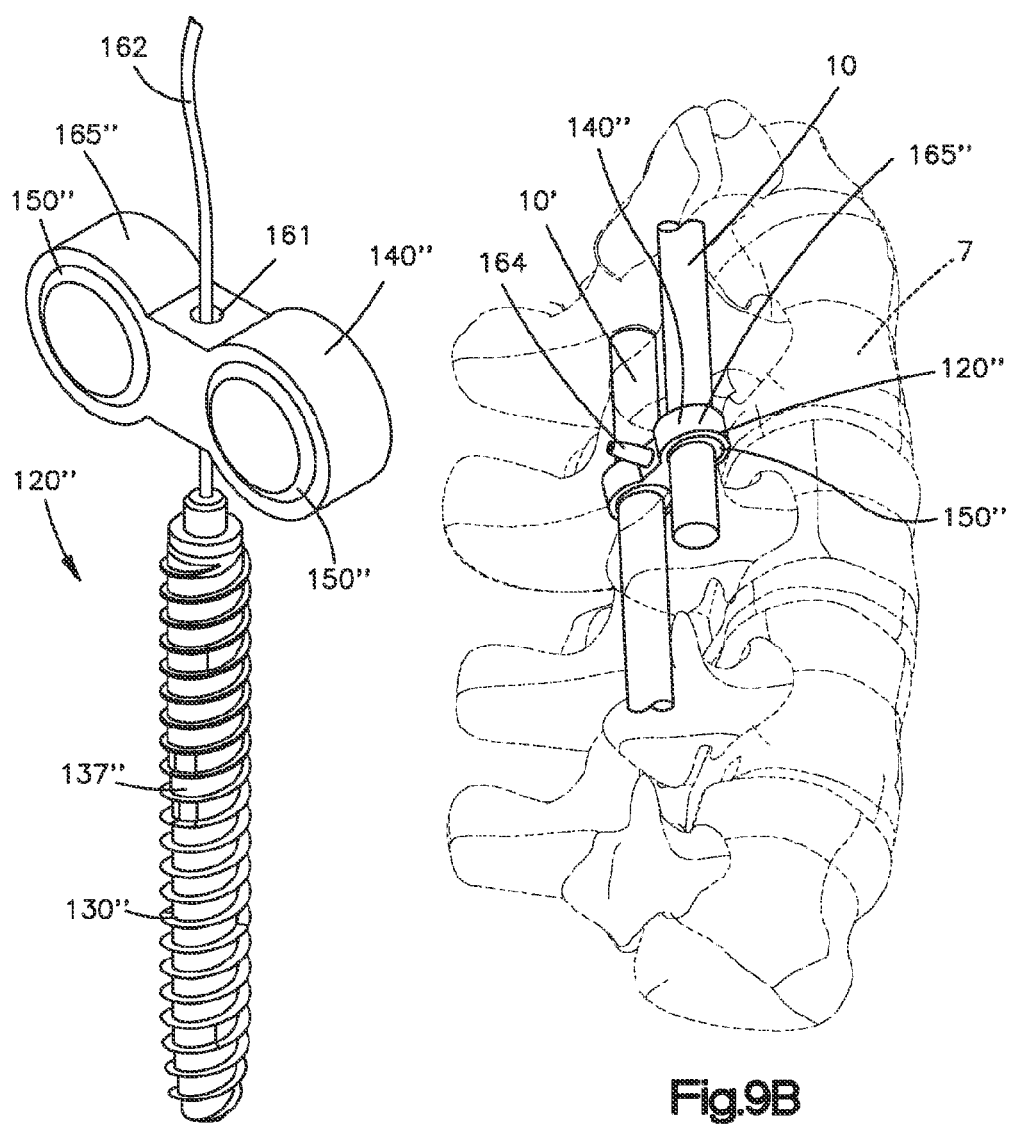

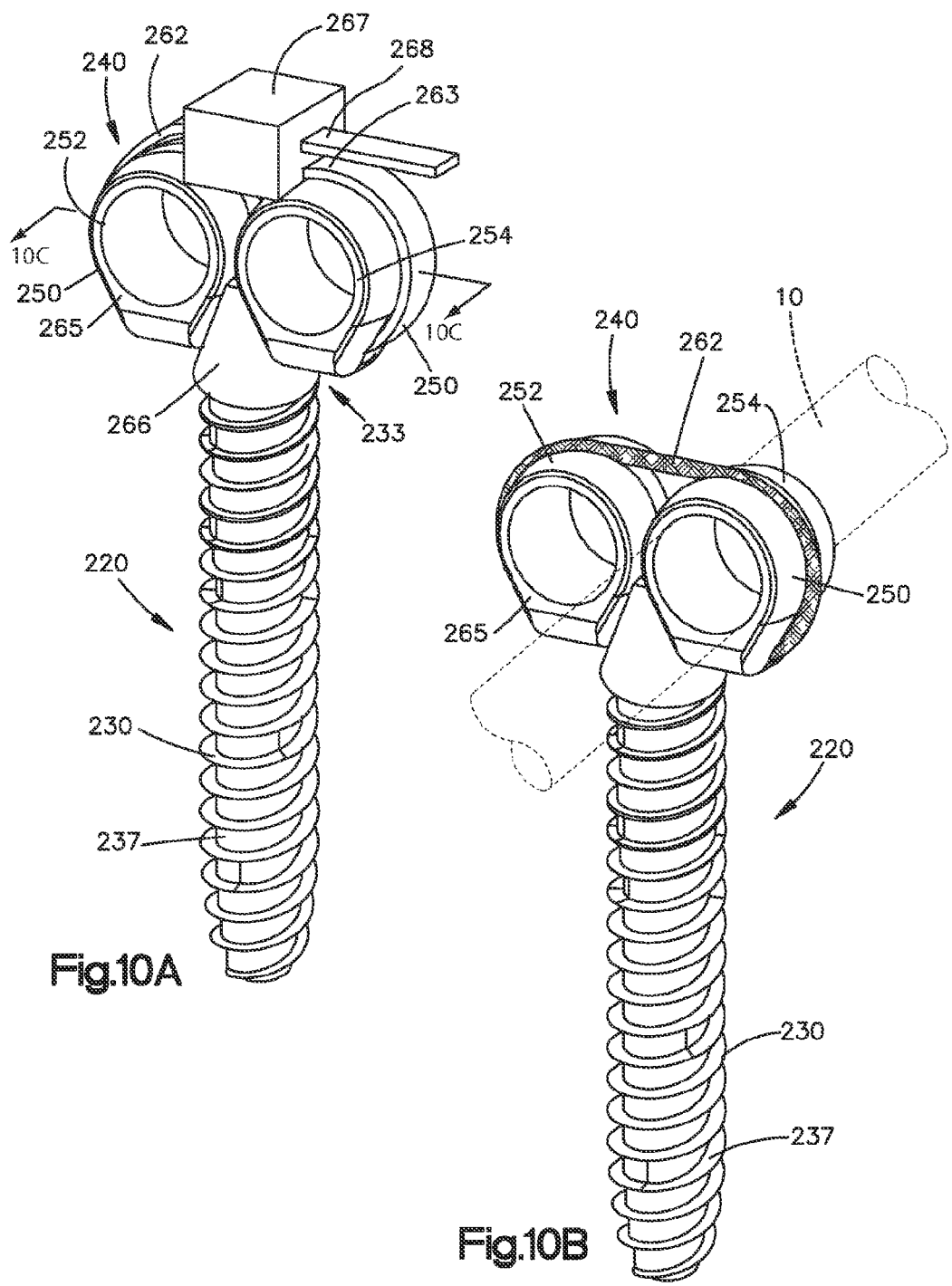

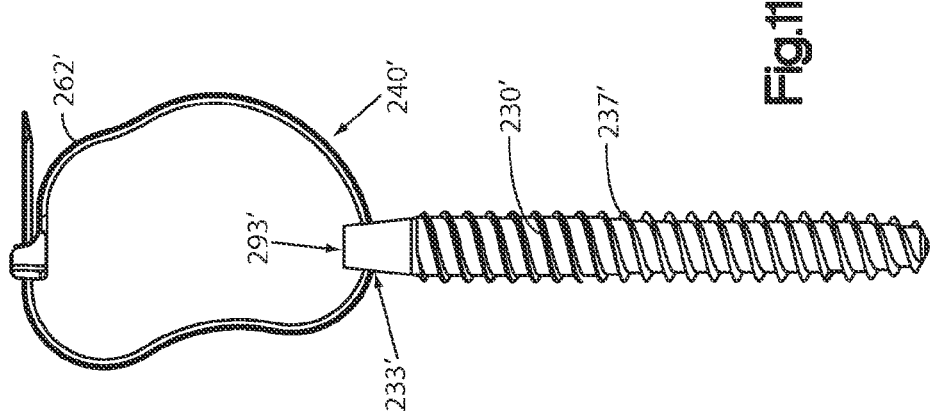
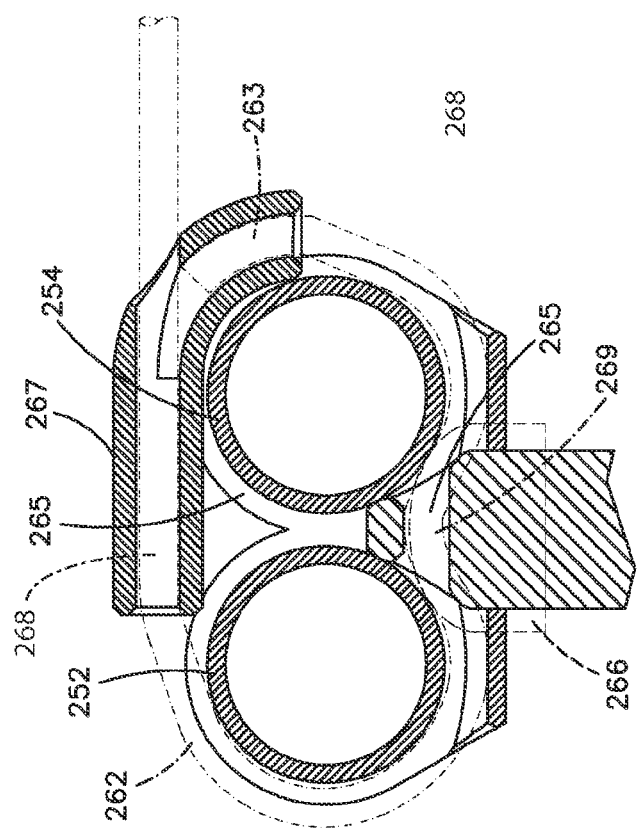

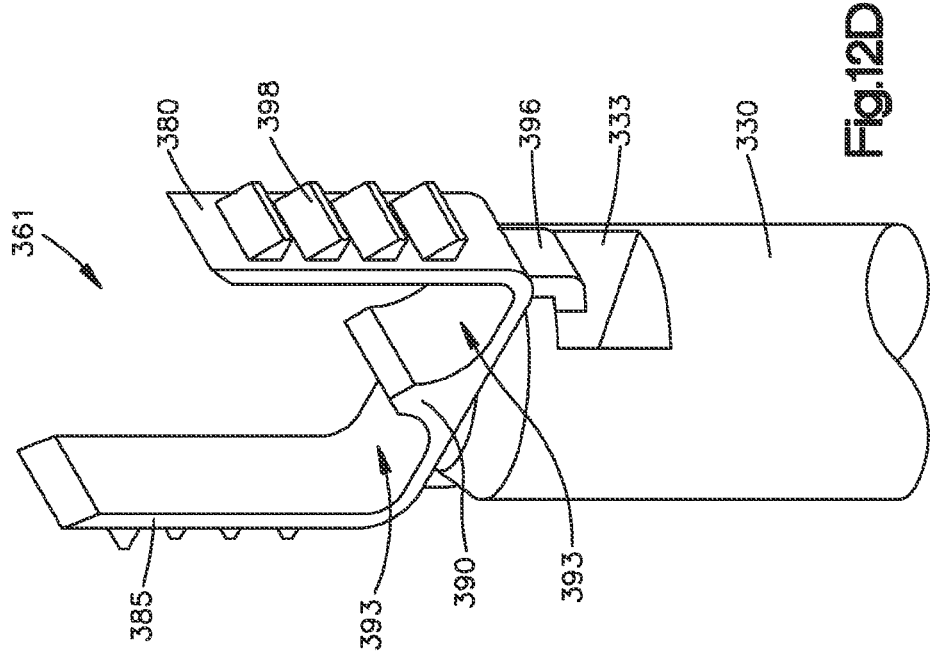
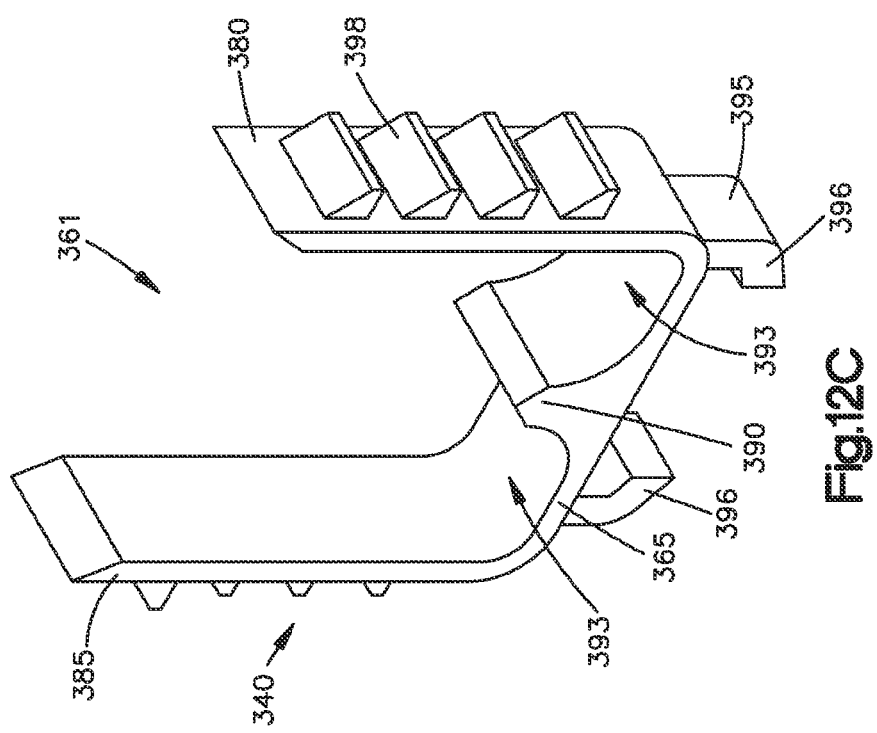

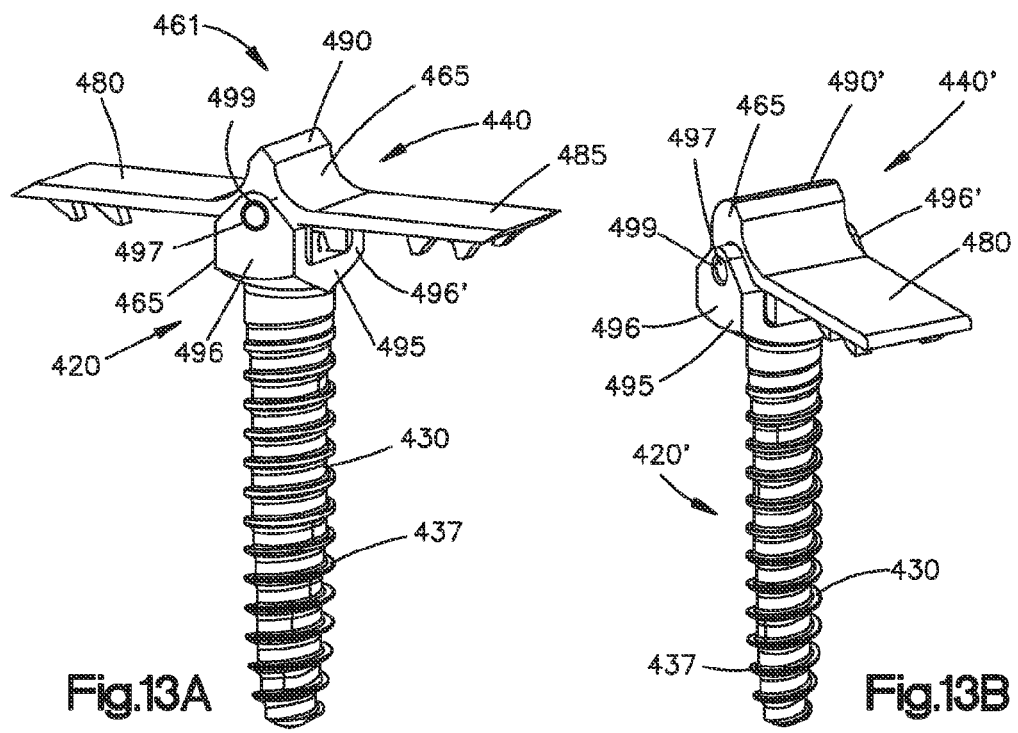
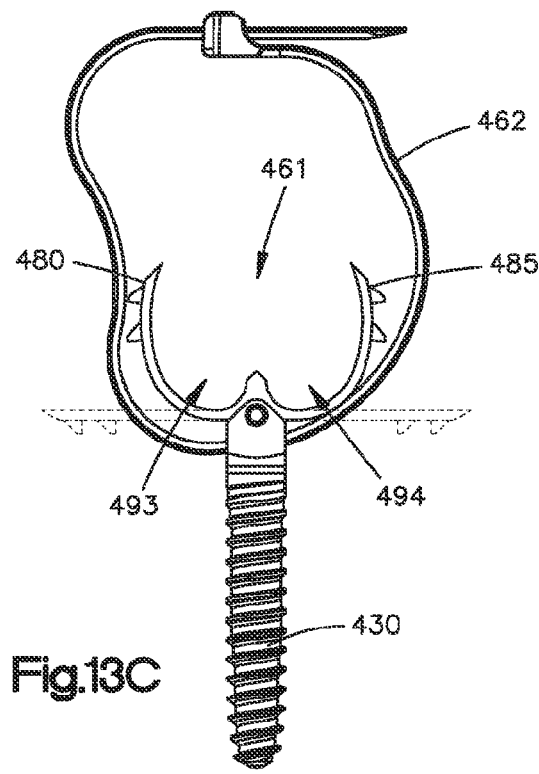

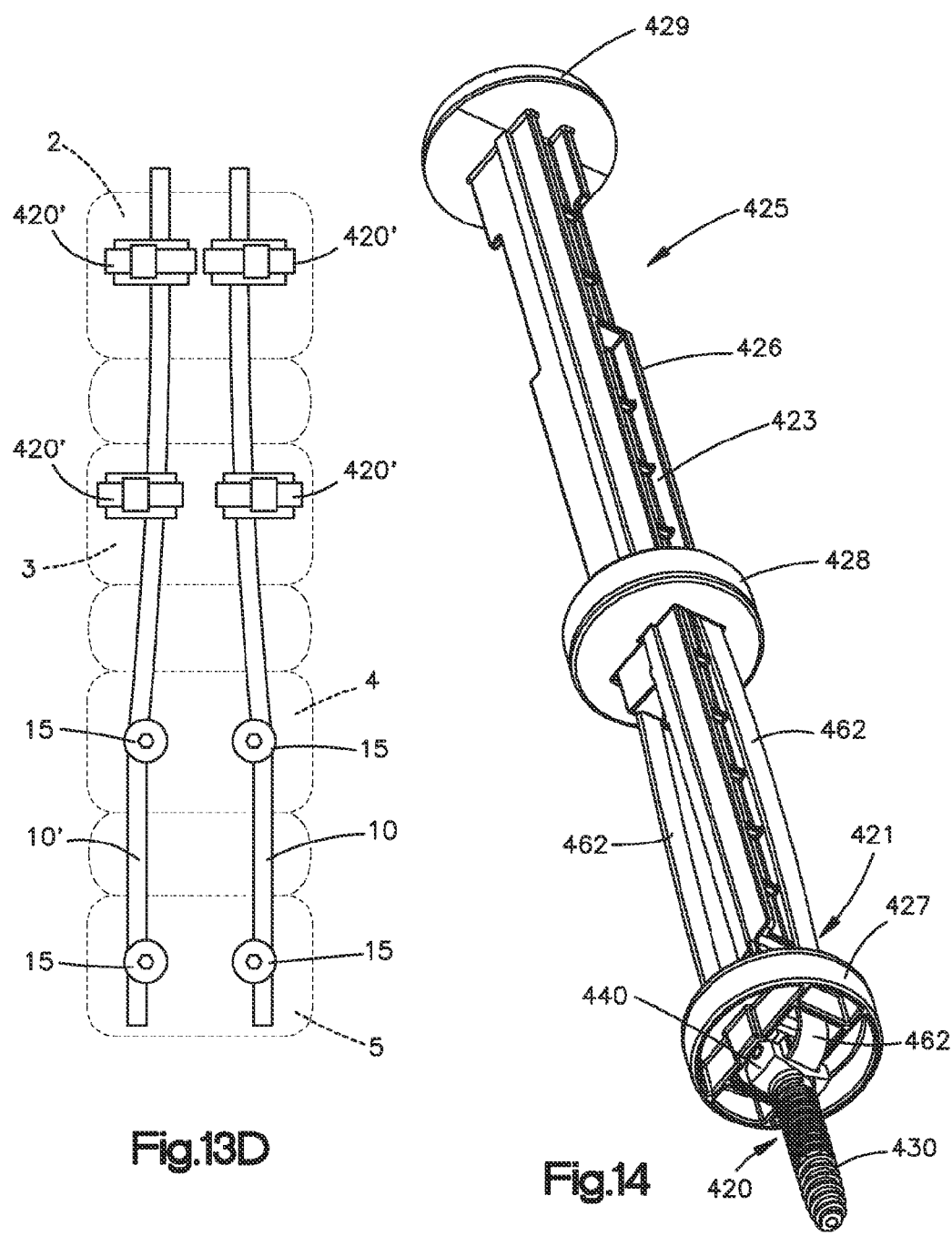

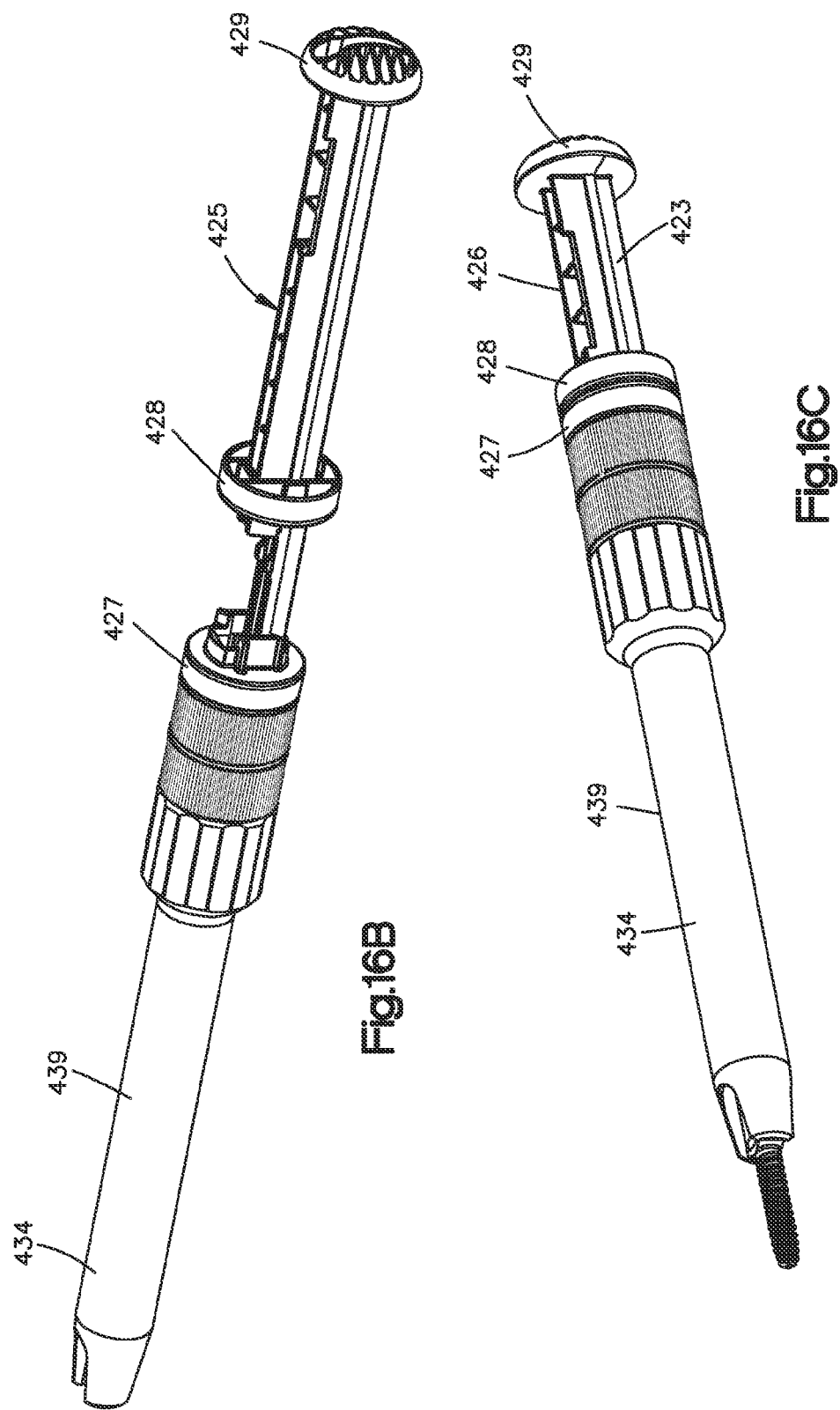

SPINAL STABILIZING AND GUIDING FIXATION SYSTEM

CROSS-REFERENCE TO RELATED APPLICATIONS

This application is the National Stage of International Application No. PCT/US2009/056692, filed Sep. 11, 2009, which claims the benefit of U.S. Provisional Application No. 61/096,453, filed Sep. 12, 2008, the disclosures of which are incorporated herein by reference in their entireties for all purposes.

BACKGROUND OF THE INVENTION

Early onset scoliosis (EOS) is a pathology that begins affecting children generally under the age of ten (10) years. Without treatment, a scoliotic spine can increase its curvature progressively, leading to severe deformation of the thorax and associated organs. Generally, two surgical options exist. The first is fusion of the scoliotic spine, which stops growth of the thorax at an early age. The second is treatment of the spine by some form of growth-guiding implants that generally must be adjusted or replaced many times over the course of the patient's childhood. Usually these further adjustments and replacements require additional surgical operations.

It is desirable to develop an implantation system and method of use that will stabilize and control the growth of the spine, and treat spinal defects such as EOS, which is easy to use.

SUMMARY OF THE INVENTION

The present invention relates to an implant system, more specifically an implant system and guiding connector for treating, repairing or stabilizing a defective or damaged spinal column, more specifically for treating early onset scoliosis (EOS).

The implant system preferably stabilizes the spinal column and directs, controls and guides the growth of the spinal column along a predetermined path. The system preferably includes one or more elongated support members, typically one or more spinal rods, that are implanted in a desirable position and which direct the growth of the spinal column by permitting the vertebrae of the spine to grow, but confine and control that growth in a particular direction and path. The system preferably further includes one or more fixed bone anchors that are firmly secured to the elongated support members, and are firmly secured to the vertebrae, and one or more guiding connectors that are firmly secured to the vertebrae but which can slide along the spinal rods. The fixed bone anchors act as anchor points for the spinal rods which preferably act as guiding rails or guiding rods. The guiding connectors are permitted to move relative to the rods and are guided by the rods to direct the growth of the spine. The guiding (or gliding) connectors enable passive growth and lengthening of the spine.

In one embodiment, the system to stabilize and guide the growth of the spinal column includes (i) one or more elongated support members, preferably longitudinal spinal rods, having a width and a length; (ii) one or more guiding connectors having a bone connecting portion and a guiding portion, the bone connecting portion configured and adapted to firmly secure the guiding connector to a vertebrae and the guiding portion having a bearing element having one or more passageways configured and adapted to receive the elongated support members, wherein the bearing element permits relative sliding movement of the elongated support members in the passageways of the bearing element; and (iii) one or more bone fixation elements having an elongated support member receiving channel, a locking mechanism and a bone anchoring portion, the bone anchoring portion configured and adapted to firmly secure the bone fixation elements to bone to provide a firm anchoring point, and the locking mechanism configured and adapted to firmly secure the elongated support member in the channel. The guiding connectors are configured to be moveable along the elongated support members preferably to permit and control the growth of the spinal column along a predetermined path.

The bone connecting portion of the guiding connector and the bone anchoring portion of the bone fixation element preferably may be one of the group of hooks, pins, tacks, stakes, nails, blades, screws and clamps. The bone connecting portion and bone anchoring portion may be monoaxial, monorotational or polyaxially rotatable with respect to other portion of the guiding connector or bone fixation element.

In one embodiment the guiding portion of the guiding connector has a front face, a back face, sides, two or more passageways extending through the bearing element from the front face to the back face, and a housing surrounding the sides of the bearing element and connecting the bearing element to the bone connecting portion, wherein an interior surface defines the passageways and preferably is formed of a polymer material. In another embodiment, the guiding connector includes a platform member, one or more bushings, a clamp member and a securing mechanism, wherein the bushings have the passageway and has an outer side surface, the platform member and clamp member substantially surrounds the side surface of the bushings, and the securing mechanism has an unlocked position that permits the bushings to polyaxially rotate with respect to the platform member and the clamp member and a locked position which fixes the position of the bushings with respect to the platform member and the clamp member. The guiding connector preferably has two bushings, each bushing having a frusto-spherical outer surface and the securing mechanism comprises a threaded set screw.

In yet another embodiment the bone connecting portion includes a post and the guiding portion includes one or more sleeve connectors, each sleeve connector having a hollow sleeve defining a bore and a recess for receipt of the post, whereby the sleeve connector is fitted over the post. A bushing forming the bearing element preferably is positioned within the bore of the sleeve and polyaxially rotatable with respect to the sleeve, and a nut configured to fit onto and mate with threads on the post connects and fixes the position of the sleeve connector and the bushing. The elongated support element is preferably slideable within the passageway of the bearing element when the bearing element is fixed with respect to the sleeve by the nut. The sleeve connector may be a C-shaped clamp having a first leg and a second leg, and wherein the nut compresses the first leg into the second leg to fix the position of the bushing relative to the sleeve while permitting the rod to slide relative to the bushing. The bushing preferably is formed from a polymer material and the sleeve is preferably formed of a material different than the bushing.

In a further embodiment the guiding connector includes a housing member having one or more openings which receives one or more bushing and a channel extending through the housing member at an angle relative to the opening, the bushings have the passageway for receiving the elongated support member and the elongated support member is slideable within the bushing when the guiding connector is implanted. A cable preferably extends from the bone connecting portion and through the channel in the housing and a crimp secures to the cable to connect the housing member to the bone connecting portion. In a still further embodiment the guiding portion further includes a platform member and one or more bushings, the bushings mounted on the platform member. A cable member having first and second ends extends at least partially around the bushings and secures the bushings on the platform member and to the bone connecting portion. The guiding portion may further include a stop member wherein the cable extends out of the stop member and wraps around at least a portion of the bushing and the cable is adjustably fixedly securable to the stop member to adjust the tension in the cable.

The guiding connector in one embodiment has a transverse opening in the bone connecting portion and the guiding portion further includes a platform member having one or more flexible wings having an inner surface and an outer surface, and a connecting portion for attaching the platform member to the bone connecting portion, wherein the wings are bendable around the elongated support members to form at least a portion of the bearing element, and wherein the guiding connector further has a cable, wherein the cable is configured to extend around the outer surface of the wings and through the opening to secure the elongated support members in the bearing element formed by the wings. Preferably the connecting portion pivotally attaches the platform member to the bone connecting portion. The platform member preferably has a protrusion member and at least two bendable wings wherein the protrusion member and wings form at least two bays for receipt of two elongated support members, the protrusion and wings constituting at least a portion of the bearing element for the elongated support members.

The system may further include instruments for use with the implants, such as, for example, a guiding connector holder. The guiding connector holder may include a distal holder having a channel, a proximal holder having a channel, and a handle portion having a shaft having a distal end and a proximal end, the proximal end having a stop member. The channel of the proximal holder is insertable over the distal end of the handle portion and slideable relative to the shaft and is configurable to secure the cable tie to the handle portion, and the channel of the distal holder is insertable over the distal end of the handle portion and slideable relative to the shaft and is configurable to secure the wings, platform member or housing of the guiding connector and cable tie to the handle portion.

The system may also include further implants such as a lateral rod connecting member having the guiding portion integrally and monolithically formed with the lateral rod connecting portion, wherein the lateral rod connecting member is adjustably securable to the bone connecting portion to adjust the position of the guiding portion and the elongated members with respect to the spinal column. Another implant may be a lateral offset connector and cable, wherein the bone connecting portion has an opening to receive the cable, the lateral offset connector forms the guiding portion and has a port for receiving the cable and two passageways forming the bearing element for receiving the elongated support members, wherein the cable connects the lateral offset connector to the bone connecting portion and the cable may be tensioned to adjust the position of the guiding portion and the elongated support elements relative to the bone connecting portion.

Other implants useable with the system include parallel connectors. In one embodiment, the parallel connector has a housing comprising a hook for securely and optionally fixedly receiving at least one of the elongated support members, and an opening for receiving a bushing, the bushing having a bore for slideably receiving the elongated support member and permitting in-situ movement of that elongated support member. In another embodiment, the parallel connector has a housing having two bores, two opening, and exterior sides, each opening extending from an exterior side of the housing into the interior of the bores, the bores sized to slideably receive the elongated support members and the openings sized smaller than the width of the elongated support member to secure the elongated support member within the bores, the housing being flexible to permit the elongated support member to pass through the opening and into the bores, the housing further having a channel in the exterior side and extending around at least a portion of the bores for receiving a cable, whereby the cable is receivable in the channel to secure the elongated support members within the bores and permit sliding motion of the elongated support members with respect to the housing.

DETAILED DESCRIPTION OF THE DRAWINGS

The foregoing summary, as well as the following detailed description of the preferred embodiments of the application, will be better understood when read in conjunction with the appended drawings. For purposes of illustrating the preferred implant system and method of use of the present invention, drawings of the preferred embodiments are shown. It should be understood, however, that the application is not limited to the precise arrangements, structures, features, embodiments, aspects, methods, and instrumentalities shown, and the arrangements, structures, features, embodiments, aspects, methods and instrumentalities shown may be used singularly or in combination with other arrangements, structures, features, embodiments, aspects, methods and instrumentalities. In the drawings:

FIG. 5 is a side view of a second preferred embodiment of a guiding connector in accordance with the present invention;

FIG. 6 is a side perspective, exploded view of the guiding connector of FIG. 5;

FIG. 7 is a side view of a third preferred embodiment of a guiding connector in accordance with the present invention;

FIG. 8 is a side perspective, exploded view of the guiding connector of FIG. 7;

FIG. 9A is a side perspective exploded view of a fourth preferred embodiment of a guiding connector in accordance with the present invention;

FIG. 9B is a side perspective view of the guiding connector of FIG. 9A connected to a vertebrae in the spine as part of a spinal stabilization and guiding system;

FIG. 10A is a side perspective view of a fifth preferred embodiment of a guiding connector in accordance with the present invention;

FIG. 10B is a side perspective view of part of a spinal stabilization and guiding system utilizing the guiding connector of FIG. 10A;

FIG. 10C is a cross-sectional view of the guiding connector of FIG. 10A taken along line 10C-10C;

FIG. 11 is a side view of a sixth preferred embodiment of a guiding connector in accordance with the present invention;

FIG. 12C is the guiding portion of the guiding connector of FIG. 12A;

FIG. 12D is a side perspective view of the guiding connector of FIG. 12A preassembled with the bone connecting portion connected to the guiding portion prior to insertion of the spinal rods;

FIG. 13A is a side perspective view of an eighth preferred embodiment of the guiding connector in accordance with the present invention;

FIG. 13B is a side perspective view of an alternative design of the guiding connector of FIG. 13A;

FIG. 13C is a side view the guiding connector of FIG. 13A with a preassembled cable tie.

FIG. 13D is a top view of the guiding connector of FIG. 13B schematically connected to vertebrae according to one method as part of a spinal stabilization and guiding system;

FIG. 14 is a perspective view of the guiding connector of FIG. 13C and cable tie assembly preassembled to an implant holder;

Figure 16A:
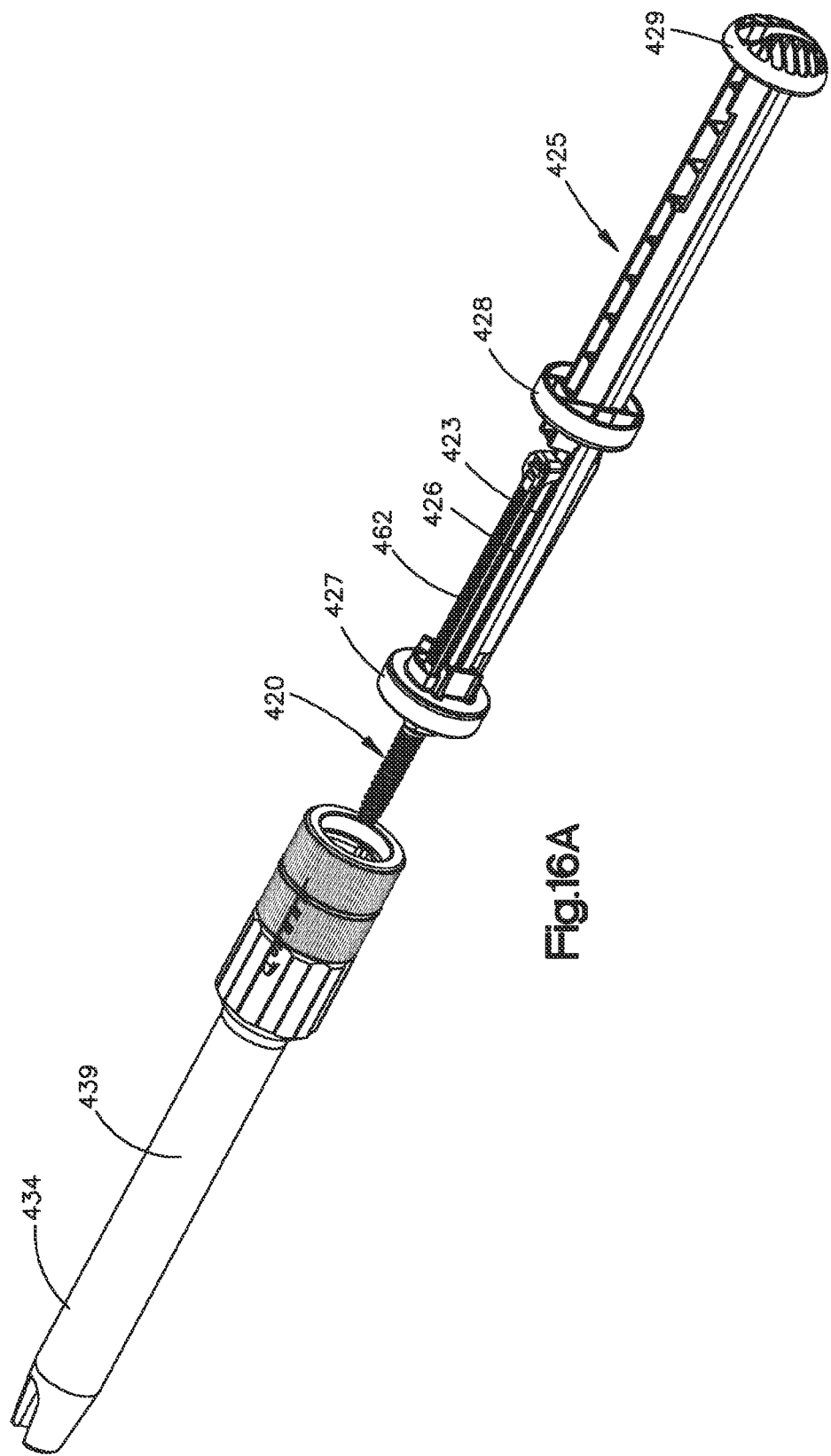
Figure 18:
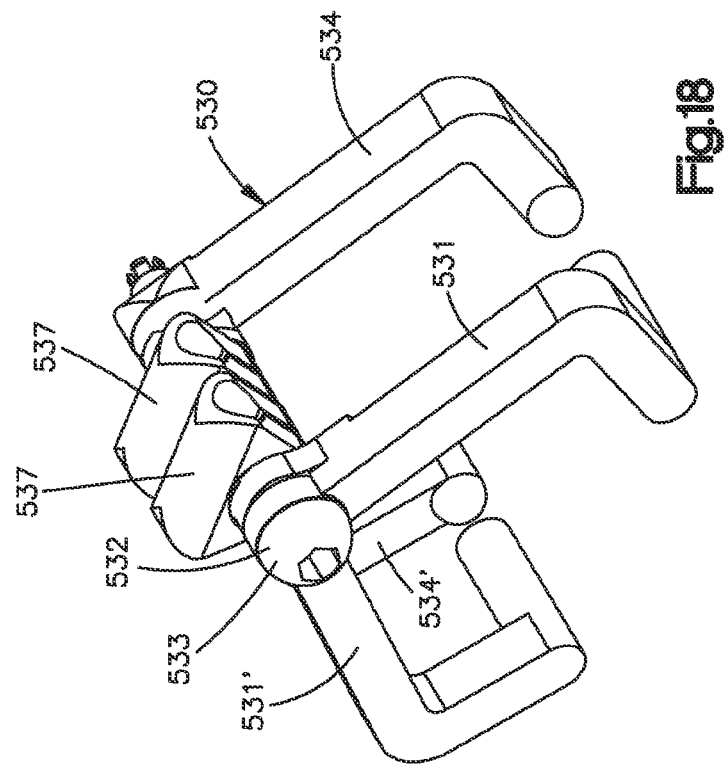
Figure 17:
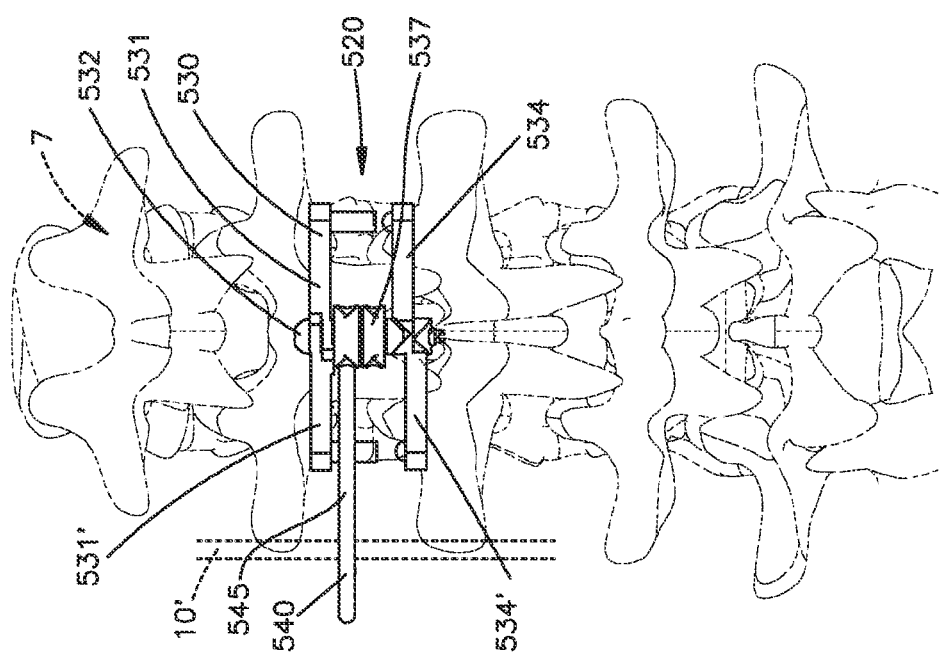
Figure 20:
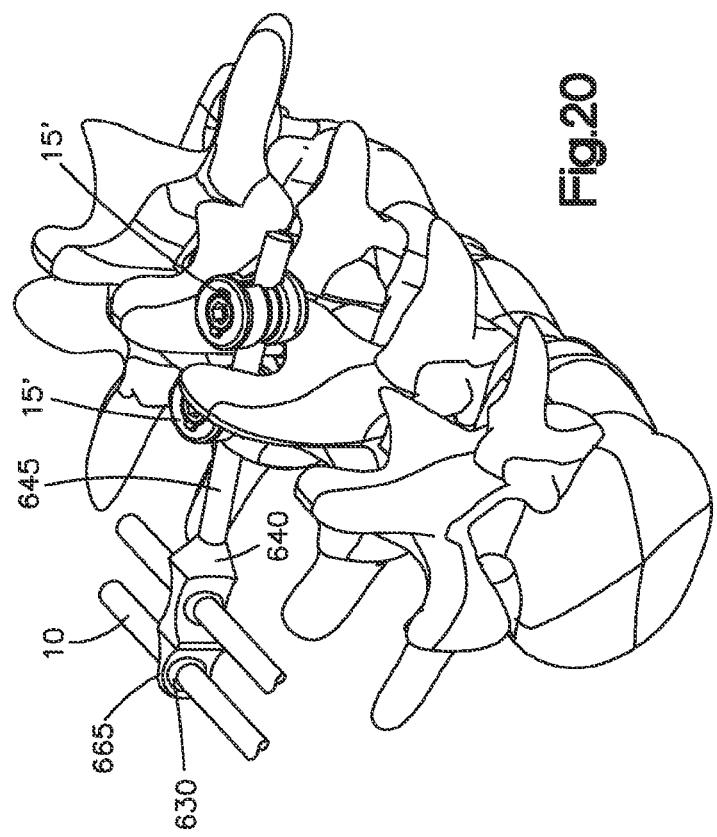
Figure 19:
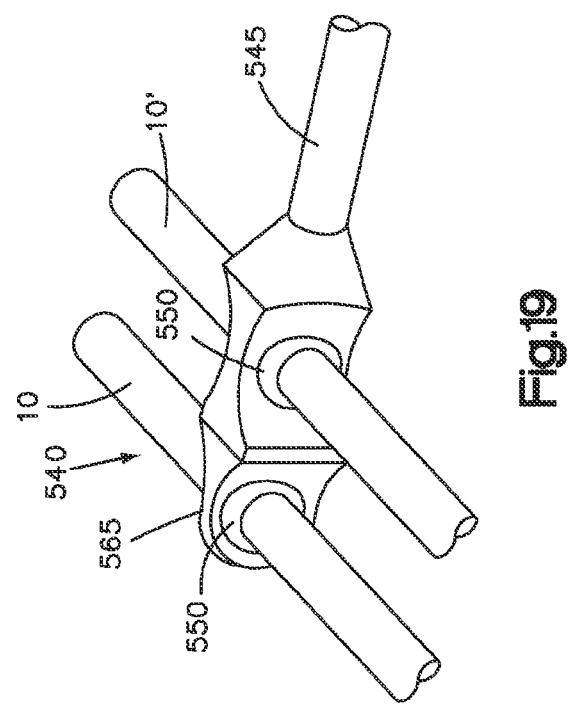
Figure 21:
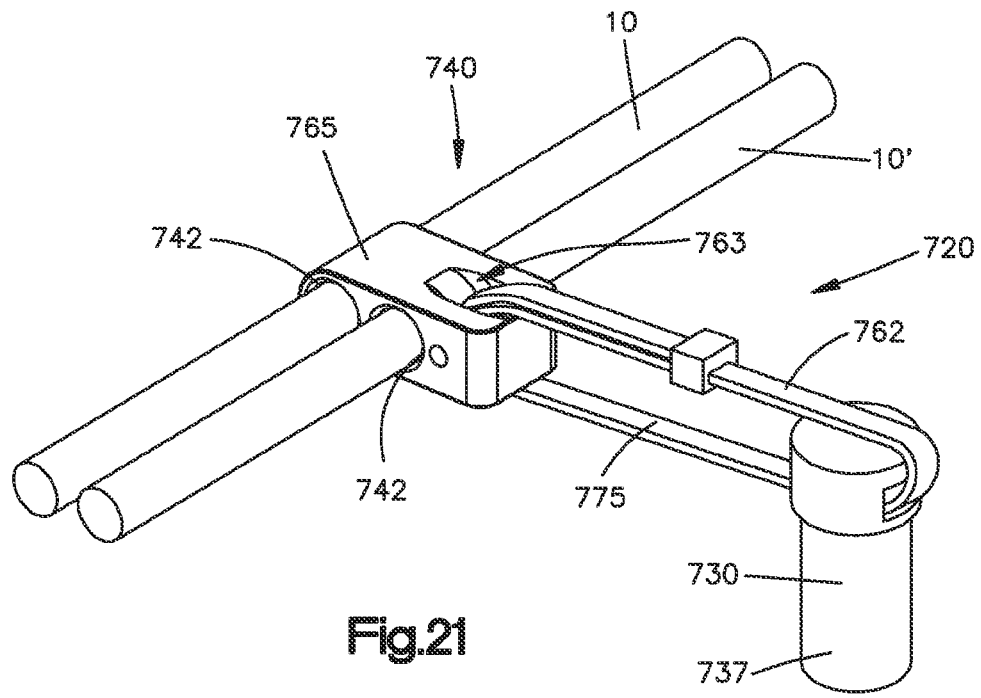
Figure 22:
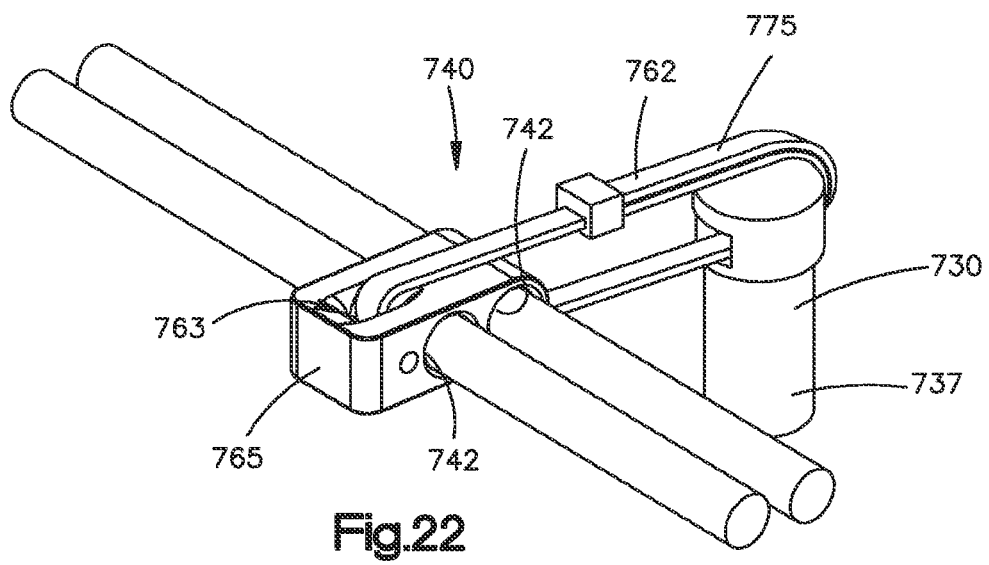
Figure 23:
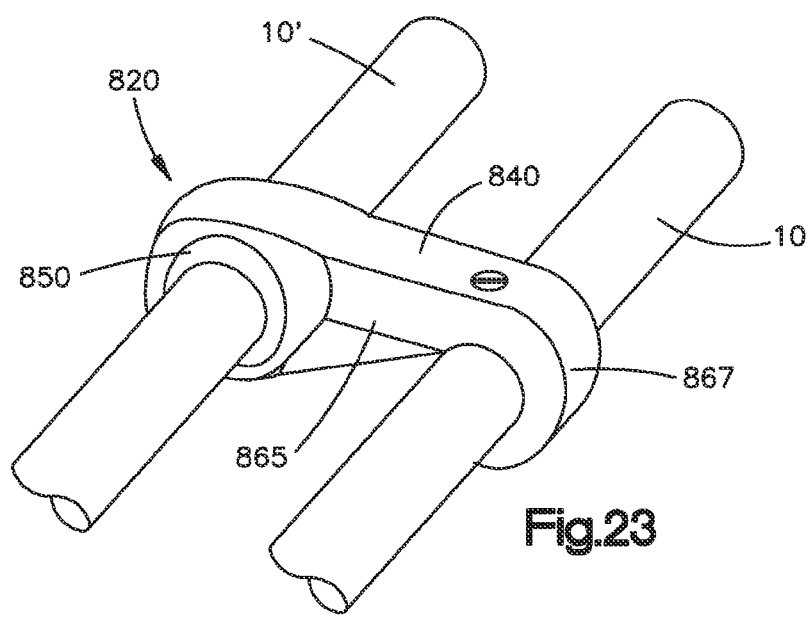
Figure 24:
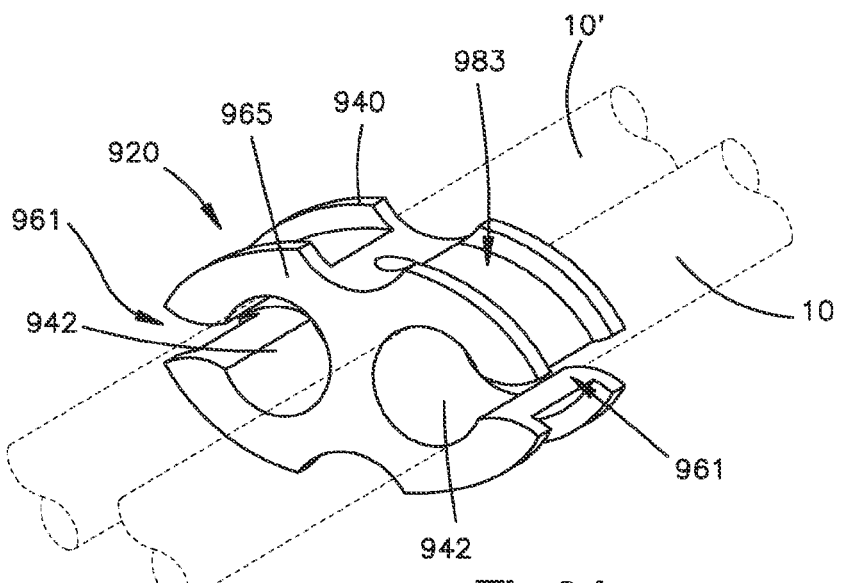

FIGS. 16A-C represents the steps of assembling the guiding connector and implant holder instrument into a screwdriver;

FIG. 17 is a top view of an ninth embodiment of a guiding connector in accordance with the present invention;

FIG. 18 is a perspective view of the bone connecting portion of the guiding connector of FIG. 17;

FIG. 19 is a perspective partial view of the guiding portion of the guiding connector of FIG. 17;

FIG. 20 is a perspective view of a tenth embodiment of a guiding connector in accordance with the present invention;

FIG. 21 is a perspective view of an eleventh embodiment of a guiding connector in accordance with the present invention configured as a lateral offset connector;

FIG. 22 is a perspective view of the guiding connector of FIG. 21 arranged differently in a stabilization and guiding system of the present invention;

FIG. 23 is a perspective view of a twelfth embodiment of a guiding connector in accordance with the present invention configured as a parallel connector; and FIG. 24 is a perspective view of a thirteenth embodiment of a guiding connector in accordance with the present invention also configured as a parallel connector.

DETAILED DESCRIPTION OF THE INVENTION

Certain terminology is used in the following description for convenience only and is not limiting. The words "right", "left", "lower", "upper", "below", "above", "top", and "bottom" designate directions in the drawings to which reference is made. The words "inwardly" or "distally" and "outwardly" or "proximally" refer to directions toward and away from, respectively, the geometric center of the spinal stabilizing device, system or the surgeon and are not meant to be limited.

The words, "anterior", "posterior", "superior", "inferior" "lateral" and "medial" and related words and/or phrases designate preferred positions and orientations in the human body to which reference is made and are not meant to be limiting. The terminology includes the above-listed words, derivatives thereof and words of similar import.

Certain preferred embodiments of the invention will now be described with reference to the drawings. In general such embodiments relate to preferred spine stabilization and growth guiding systems including preferred guiding connectors and related instruments by way of non-limiting example for use in the treatment of the spine.

Referring to FIGS. 1-4, a first preferred embodiment of a spine stabilizing and guiding system 100 is shown implanted in the spinal column 7 according to three different attachment configurations. The spine stabilization system 100 is preferably used in the spine, and may be used in the cervical, thoracic and/or lumbar regions of the spine. The spinal stabilization system 100 may have particular application in the correction of early onset scoliosis. While the system 100 is described as generally for use in the spine, it will be appreciated that the system 100 may have other uses and may be used as a bone fixation or stabilization system and device for use on other bones or joints, such as, for example, the shoulder, elbow, wrist, hand, finger, cranium, mandible, ribs, hip, knee, ankle, foot, toe, extremities, and may be used in non-orthopedic and/or non-medical applications.

The spinal stabilization system 100 may include (1) one or more elongated support elements 9, such as, for example, longitudinal spinal rods 10, (2) one or more standard vertebral fixation devices 15 for securely connecting a vertebra to the elongated support elements, such as, for example, pedicle screws (monoaxial, monorotational, polyaxial screws), lamina and pedicle hooks (monoaxial, monorotational, and/or polyaxial hooks), or other bone anchors which may be firmly secured to one or more vertebrae preferably to act as anchor points, (3) one or more guiding connectors for anchoring in vertebra and for guiding and controlling the movement of the vertebrae along the elongated support elements 9 so that the vertebra of the spinal column 7 may move along a growth path to permit growth of the spinal column 7 and thorax, (4) one or more lateral connectors for laterally offsetting the guiding connectors from the axis of the spine; and (5) one or more parallel connectors for permitting relative motion of elongated support members.

It should be understood that the elongated support element 9 is typically a spinal rod 10 but that the system is not limited to use with spinal rods and any elongated support member of any shape and configuration is contemplated. The support member 9 may include solid, non-solid, hollow, partially solid, flexible or dynamic spinal rods 10. The spinal rods 10 for use in the stabilization system 100 may be standard spinal rods commonly used in spinal stabilization surgeries, generally of approximately 6 mm in diameter, although it may be preferred for pediatric uses, to which the present system may particularly be adapted and designed, to utilize 5.5 mm spinal rods. Alternatively or additionally, the system may utilize dynamic spinal rods which may permit flexing of the spinal rod 10 implanted within a patient.

The elongated support members 9, referred to herein interchangeably as spinal rods, are utilized to act as guide rails to direct the growth of the spine. That is, in one preferred embodiment, the surgeon implants the spinal rods so that they are configured to correspond to a desired growth path for a patient. The spinal rods are preferably fixedly secured to one or more vertebrae which act as anchor points. The spinal rod is implanted to correspond to the desired growth path for the spine by supplying or bending the spinal rod to a desired configuration. Guiding connectors are then preferably connected to other vertebrae and are permitted to move and slide along the spinal rods to enable passive growth and lengthening of the spine. The spinal rods act as rails which direct and control the motion of the guiding connectors and thus control the direction of growth of the vertebrae to which they are attached. The fixed anchor points for the stabilizing and guiding system may be located at the ends or in the middle of the construct.

It will be appreciated that the bone anchors and/or guiding connectors may be connected to the vertebrae by polyaxial, monoaxial, or monorotational screws, hooks, pins, tacks, nails, stakes, blades or other types of bone anchor mechanisms, or clamps. The system may optionally include one or more transconnectors 12 for attaching two parallel spinal rods 10, 10' implanted in the spinal column 7 of a patient.

Figure 1:
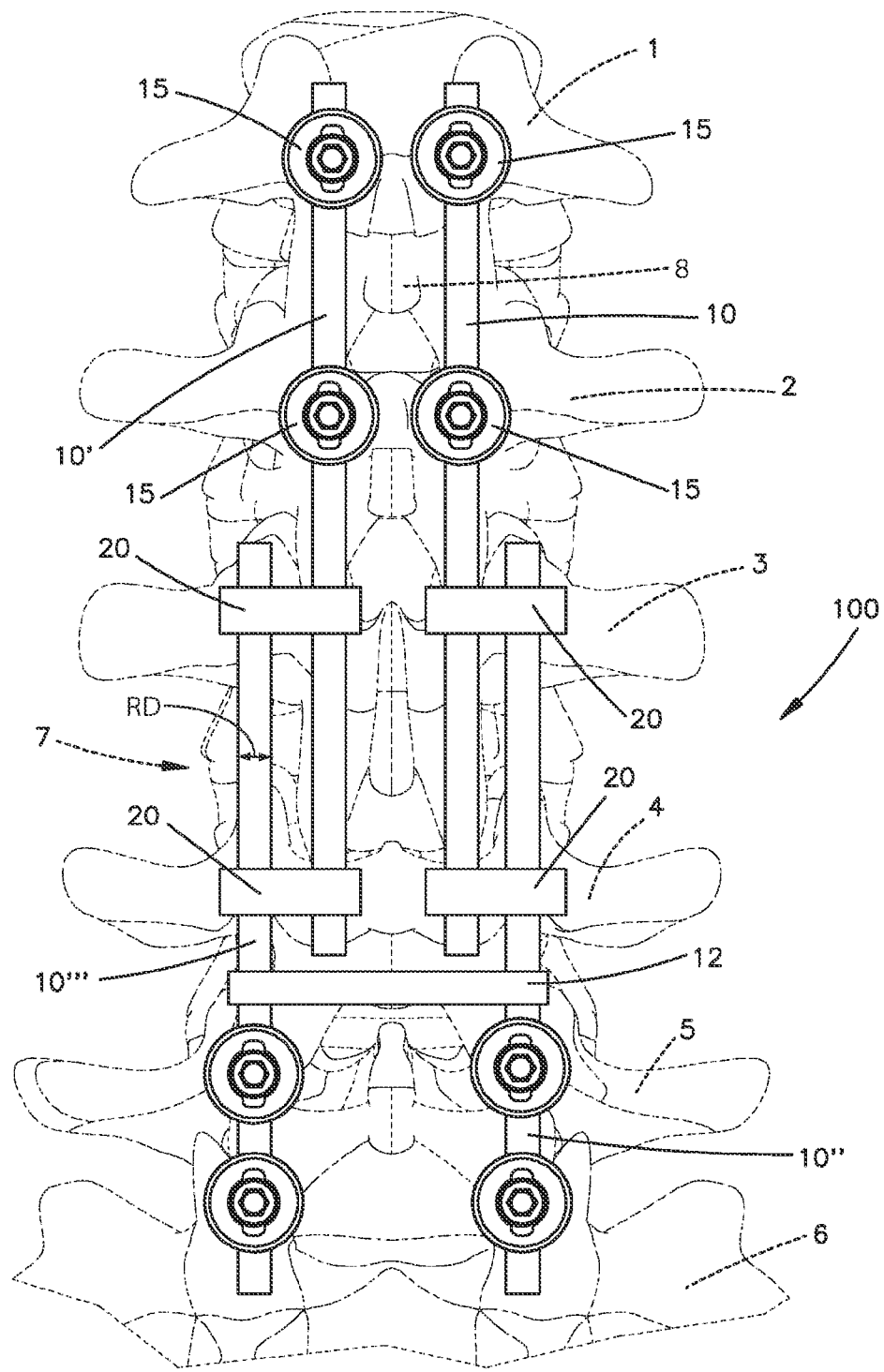
FIG. 1 is a top plan view of a spinal stabilization and guiding system of the present invention for directing the growth of a spinal column along a predetermined path implanted in the spinal column of a patient in accordance with a first attachment configuration.

Referring to FIG. 1, a first preferred spinal stabilization system 100 and attachment configuration includes a first pair of elongated support members 9, typically spinal rods 10, longitudinally placed on the posterior spine on either or both sides of the spinous process 8 of a spinal column 7. Rods 10, 10', 10", 10'" are fixedly attached to vertebra by bone fixation elements 15, e.g., standard pedicle screws 15. The body portion of the standard pedicle screw typically has a rod-receiving channel and receives a locking cap or mechanism to secure the spinal rod 10, 10' to the pedicle screw 15. A pedicle screw useable in the spinal fixation system 100 is disclosed in International Patent Appln. No. PCT/US2008/070670, entitled "Polyaxial Bone Fixation Element", filed Jul. 21, 2008, the entire contents of which are incorporated by reference herein. The bone fixation element 15 may have a body portion that is pivotal with respect to the bone anchor, commonly known as polyaxial pedicle screws or polyaxial hooks. Monoaxial or monorotational screws and/or hooks are also contemplated for use with the spinal stabilization and guiding system 100. Other bone fixation elements are also contemplated for use with the stabilization and guiding system 100.

As shown in FIG. 1, the system 100 may be anchored at superior vertebrae 1, 2 and inferior vertebrae 5, 6 via standard pedicle screws 15 which secure the spinal rods 10, 10', 10", 10'" in a fixed position relative to the attached vertebrae. In the example shown in FIG. 1, four (4) standard pedicle screws 15 are implanted in vertebrae 1 and 2, and four (4) standard pedicle screws 15 are implanted in vertebrae 5, 6. Two spinal rods 10, 10' extend substantially parallel from the superior vertebra 1, 2 toward the inferior vertebrae 5, 6, and two spinal rods 10", 10'" extend substantially parallel from the inferior vertebrae 5, 6 toward the superior vertebrae 1, 2 so that in total four (4) spinal rods are utilized. The two spinal rods 10, 10' that extend from the superior vertebra 1, 2 traverse the two intermediate vertebrae 3, 4, while the two spinal rods 10", 10'" that extend from inferior vertebrae 5, 6 also traverse the two intermediate vertebrae 3,4 so that all four (4) rods 20 preferably extend over at least a portion of the intermediate vertebrae 3, 4. The four (4) rods 10, 10', 10", 10'" preferably are substantially parallel and provide for telescopic extension of the system and permit growth of the spine and relative movement of the vertebra 2, 3, 4, 5. The construct of FIG. 1 is referred to as a parallel construct. The parallel construct is anchored distally and proximally and in the middle telescopic elongation is permitted by guiding connectors 20.

Gliding or guiding connectors 20 are attached to the intermediate vertebrae 3, 4. Guiding connectors 20 preferably permit growth and lengthening of the spine. In particular, the spacing between the adjacent vertebrae can change as the patient grows as the spinal rods 10, 10', 10", 10'" can slide and telescope with respect to the guiding connector 20.

Figure 2:
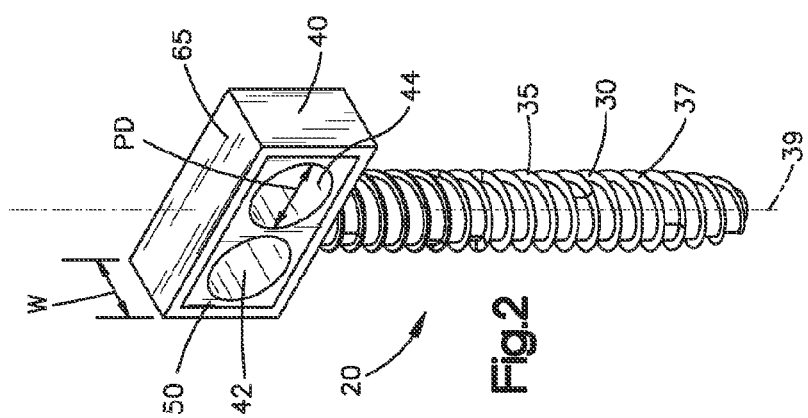
FIG. 2 is a perspective view of a first preferred embodiment of a guiding connector in accordance with the present invention that may be used in the stabilization system of FIG. 1.
Figure 12A:
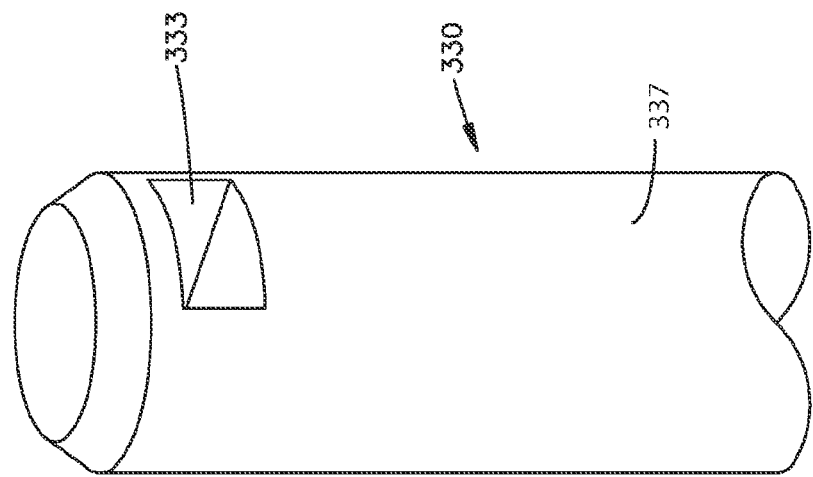
FIG. 12A is a side perspective view of a seventh preferred embodiment of a guiding connector in accordance with the present invention.
Figure 12B:
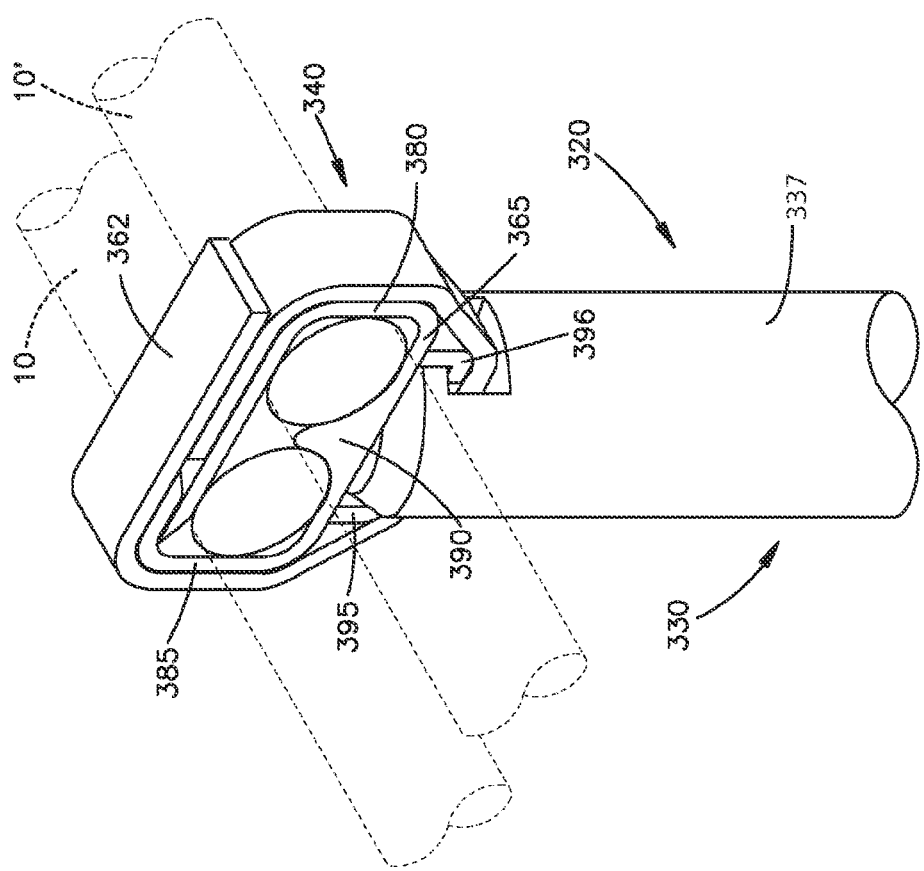
FIG. 12B is the bone connecting portion of the guiding connector of FIG. 12A.
Figure 15:
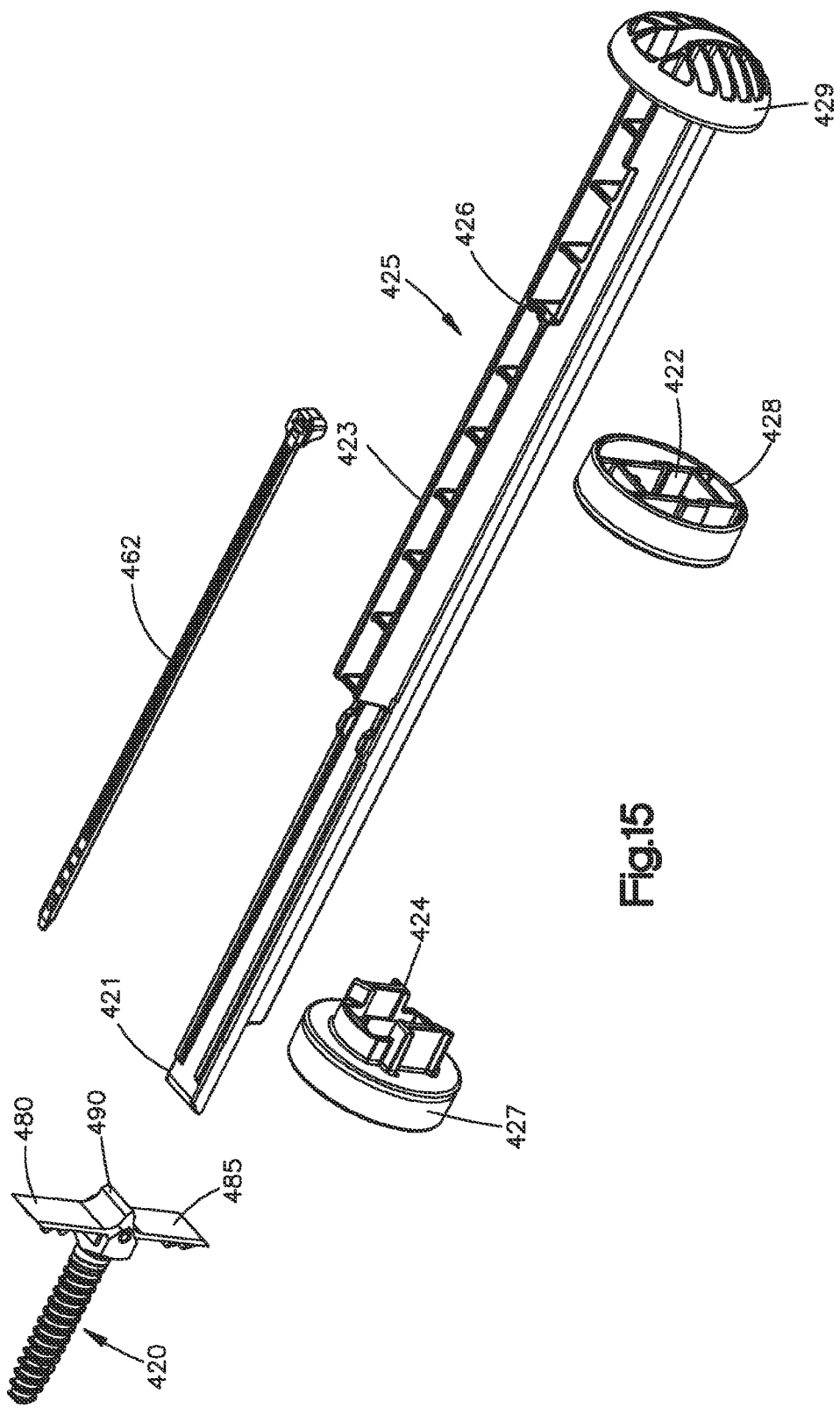
FIG. 15 represents the component parts of the guiding connector and the implant holder of FIG. 14.

The guiding connector 20 preferably should be firmly secured to one or more vertebrae so the guiding connectors can slide and glide with respect to the spinal rods as the spinal column grows. Guiding connector 20 preferably includes a bone connecting portion 30 and a rod guiding portion 40. In the embodiment of FIG. 2, the bone connecting portion 30 is a screw 35 having a screw shaft portion 37 having a longitudinal axis 39. While bone connecting portion is illustrated and described as a screw 35 in the preferred embodiment of FIG. 2, it will be appreciated that the bone connecting portion 30 may include polyaxial, monoaxial or monorotational screws, hooks, pins, blades, stakes, nails, clamps, or other types of bone anchoring mechanisms now known or later discovered.

The guiding portion 40 of the guiding screw 35 includes at least one bearing element 50 having one or more passageways. The guiding portion 40 of the embodiment of FIG. 2 preferably has two (2) passageways 42, 44 that are inclined at an angle, preferably generally perpendicular, to longitudinal axis 39 of the shaft 37 of the screw 35. Passageways 42, 44 extend through the guiding portion 40 to enable the spinal rods to be inserted there through. Passageways 42, 44 are sized and dimensioned to permit sliding movement of the spinal rods through the guiding portion 40 when the system is implanted in a patient. In this manner, passageways 42, 44 preferably have a diameter PD that is close to the diameter RD of the spinal rods 10, 10', 10", 10'" and preferably 42, 44 serve as a bearing sleeve. The larger the width W of the passageways (e.g., the greater the length of the bearing sleeve), potentially the easier the rod may slide and move in the passageway. Exemplary widths W of the bearing element 50 are about 1 mm to about 10 mm. Other dimensions for the width W of the bearing element 50 are contemplated and will depend upon a variety of factors.

Alternatively, the guiding portion 40 may have two passageways 42, 44 that that extend substantially perpendicular to the longitudinal axis of the shaft 37 but are open at the top portion to form a channel 55, 57 which communicates with the bores 52, 54. The channel 55, 57 enables a surgeon to snap in the spinal rods 10, 10' from the top of the guiding connector 20 to facilitate ease of assembly of the system 100 (see FIG. 24). The channels 55, 57 are preferably less than the width or diameter RD of the spinal rod 10 so that the spinal rod 10 is constrained by the guiding portion 40 and is not easily detachable from the guiding connector 20. After the spinal rod is placed in passageways 42, 44, member 58 or cable or cable tie 62 may close the channels 55, 57 to prevent the spinal rod 10 from being dislodged from the guiding portion 40 when implanted in the patient.

The materials of construction for the guiding portion 40, and specifically the bearing element 50 are preferably chosen to minimize friction and wear between the interior surface 43, 45 forming the passageways 42, 44 and the spinal rods 10, 10', 10", 10'". The material forming the passageways 42, 44 or at least the surface 43, 45 which interacts with and contacts the rods 10, 10', 10", 10'" may be formed from PEEK, or ultra high molecular weight polyethylene (UHMWPE). The rod and/or bone connecting portion 30 may preferably be formed of metals such as, for example, titanium, titanium alloys (Ti-6Al-7Nb), stainless steel, cobalt chromium, Nitinol, etc. The spinal rods and/or interior surface 43, 45 of the passageways 42, 44 may be polished or coated, such as with polytetrafluoroethylene for example, to reduce the coefficient of friction to enhance the gliding and/or sliding characteristics of the spinal rods 20 through the passageways 42, 44.

The guiding portion 40 may include a housing 65 that at least partially surrounds, and may preferably completely surround the sides of the bearing element 50 preferably to provide support and strength to the bearing element 50. The housing 65 may be connected to the bone connecting portion 35. The housing 65 may be connected to the bone connecting portion 35 in a variety of manners including, but not limited to, bonding, welding, gluing, press fit, threading connection, integral and monolithic, etc. The housing may be formed of a biocompatible metal or metal alloy or other materials. The passageways 42, 44 and the bearing element 50 preferably are fixed with respect to the housing 65 and the bone connecting portion such that the pathway for the spinal rod is not adjustable before, during or after implantation of the guiding connector 20.

In the stabilization and guiding system 100, the spinal rod 10 can slide within the passageway 42 located in the guided connector 20 implanted in vertebrae 3, and slide through the passageway 42 of the guiding connector 20 implanted in vertebrae 4, as a result of vertebrae 2 moving relative to vertebrae 3 and 4 (or vertebrae 3 moving relative to vertebrae 4). Additionally, the spinal rod 10' preferably is permitted to move and slide in passageway 44 of the guiding connector 20 implanted in vertebrae 3 and the passageway of guiding connector 20 implanted in vertebrae 4 as a result of vertebrae 2 moving relative to vertebrae 3 and 4 (or vertebrae 3 moving relative to vertebrae 4). The spinal rod 10" is permitted to move and slide within passageway 44 of the guiding connector 20 implanted in vertebrae 3, and within the passageway 44 of the guiding connector 20 implanted in vertebrae 4 as a result of vertebrae 5 moving relative to vertebrae 3 and 4 (or vertebrae 3 moving relative to vertebrae 4). Additionally, spinal rod 10''' preferably is permitted to move and slide within passageway 44 of the guiding connector 20 implanted in vertebrae 3 and passageway 44 of the guiding connector 20 implanted in vertebrae 4 as a result of vertebrae 5 moving relative to vertebrae 3 and 4 (or vertebrae 3 moving relative to vertebrae 4). Thus, the system permits the vertebrae, which are connected to the guiding connectors, to move along a path defined by the shape and configuration of the implanted spinal rods.

The guiding portion 40 is designed and configured to move along the spinal rods which preferably constrain and restrict the movement of the guiding connectors in a particular path and/or direction. Since the guiding connector is attached, preferably firmly attached, to the vertebrae, the growth and movement of the vertebrae and the growth of the spine is permitted, but preferably is constrained and limited to the path permitted and defined by the implanted spinal rods. The spinal rods 10, standard fixation devices 15 (e.g., pedicle screws) and guiding connectors 20 can be configured in the spinal column 7 in various configurations, such as, for example, the configuration of FIG. 1 where the standard fixed pedicle screws 15 which anchor and fix the spinal rods 10, 10', 10", 10''' with respect to the vertebrae are located and connected to the vertebrae at the ends of the implanted system 100 while the guiding connectors 30 are connected to the intermediate vertebrae 3, 4 located between the fixed end vertebrae.

While the system 100 has been shown as having fixed bone anchors 15 in two adjacent vertebrae at the ends of the implanted system, the fixed bone anchors 15 can be attached to a single vertebrae using one or more pairs of fixed bone anchors 15, and/or the fixed bone anchors can span one or more vertebrae. In addition, while system 100 in FIG. 1 has been illustrated and described as being implanted laterally on both sides of the spinous process 8, it is contemplated that the system may be utilized either on the right lateral side or the left lateral side of the spinous process 8.

Figure 3:
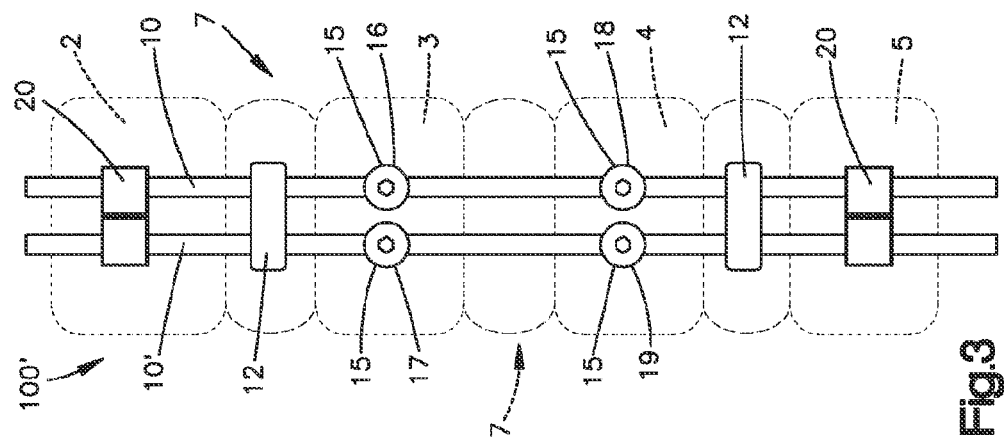
FIG. 3 is a top plan view of a schematic representation of a spinal stabilization and guiding system of the present invention using a guiding connector in accordance with a second attachment configuration.

Referring to FIG. 3, another configuration of the stabilizing and guiding system 100' is shown where in this case the standard pedicle screws 15 are fixed to the intermediate vertebrae 3, 4, while the guiding connectors 20 are attached to the end vertebrae 2, 5. More specifically, two standard pedicle screws 16, 17 are fixed to intermediate vertebrae 3 while two standard pedicle screws 18, 19 are attached to adjacent vertebrae 4. A first spinal rod 10 is fixedly connected to pedicle screws 16, 18 while a second spinal rod 10' is fixedly connected to standard pedicle screw 18, 19. Spinal rods 10, 10' preferably are curved and correspond to the appropriate spinal curvature for a healthy normal spinal section and assists in defining the path of growth for the spinal vertebrae.

Guiding connectors 20 are connected to the first vertebrae 2 and the last vertebrae 5. The guiding connectors 20 are preferably in the form of screws 35, having a guiding portion 40 as shown in FIG. 2 but may be any of the embodiments described and illustrated herein and modifications thereof. The bearing element 50 of the guiding portion 40 may have a plurality of passageways 42, 44 for receiving spinal rods 10, 10', or each end vertebrae 2, 5 may include one or more guiding connectors 20 each having a bear element 50 which contains only a single passageway 42 for receiving a single spinal rod.

The system and construct 100' of FIG. 3 preferably fixes the apex of a scoliotic curve. The term "apex", as used herein denotes the center of curvature of a scoliotic deformity and lies in the middle of the curve. The apex preferably would include the origin of the pathology, and treating it actively preferably means focusing on the cause of deformation. By fixing the apex, the center of the curvature would become fused and immobile. The end vertebrae 2 and 5, however, would be able to move relative to the intermediate vertebrae 3, 4 and the system 100' would direct the path of that movement along the direction and curvature of the spinal rods 10, 10'.

Figure 4:
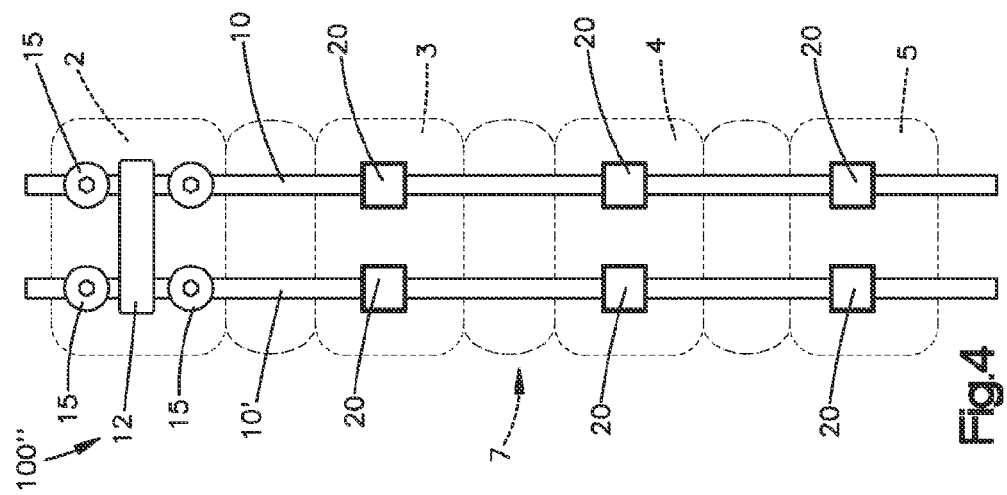
FIG. 4 is a top plan view of a schematic representation of a spinal stabilization and guiding system of the present invention using a guiding connector in accordance with a third preferred attachment configuration.

In another configuration of stabilizing and guiding system 100" as illustrated in FIG. 4, the system 100" uses standard pedicle screws 15 in end vertebrae 2 to fix the spinal rod 10, 10' with respect to the vertebrae 2 at only one end of the construct/system. The system and construct 100" of FIG. 4 is intended to fix the curvature of the spinal column 7 at the end (vertebrae 2) and permit spinal growth away from the vertebrae 2. Specifically the system 100" of FIG. 4 includes spinal rods 10, 10' connected to standard pedicle screws 15 fixed in vertebrae 2. Spinal rods 10, 10' extend through guiding connectors 20 secured to vertebrae 3, 4 and 5. The spinal rods 10, 10' extend through the passageways 42, 44 located within the bearing element 50 of the guiding portion 40 of the guiding connectors 20. The guiding connectors 20 are permitted to move along the spinal rods 10, 10' to permit and enable passive growth and lengthening of the spine preferably along a predetermined path defined by the spinal rods 10, 10'.

Referring to FIGS. 5 and 6, a second preferred embodiment of a guiding connector 120 is shown. The guiding connector 120 preferably comprises a bone connecting portion 130 and a guiding portion 140. The bone connecting portion 130 is preferably in the form of a bone screw 135. Alternatively, however, the bone connecting portion 130 may be, for example, a hook, pin, blade, nail, tack, stake or other fasteners, such as, for example, a clamp, an implant, etc.

The guiding portion 140 preferably comprises platform member 152, one or more bushings 150, a clamp member 160, and a set screw 170. In the embodiment of FIGS. 5 and 6, the guiding connector 130 includes two (2) bushings 153, 154 although embodiments with only one bushing 150 or more than two bushings 150 are contemplated. The guiding connector 130 preferably incorporates one or more bushings 150 that preferably have a frusto-spherical outer surface 151 that preferably moves and adjusts angularly within the platform member 152 and the clamp member 160 to permit polyaxial movement of the bushing 150 relative to the platform member 152. The bushings 150 preferably have a bore 142 sized to permit the spinal rod 10 to be inserted through and slide with respect to the guiding portion 140. The material of the inner surface 141 of the bore 142 preferably is formed of a material chosen to minimize friction and wear between the bushing 150 and the spinal rods 10, 10', 10", 10'". Preferred materials for the bushing 150 include polymers such as PEEK and ultra high molecular weight polyethylene (UHMWPE). Preferred materials for the spinal rods 10, 10', 10", 10'" include titanium alloy (TI-6AL-6NB), cobalt chromium, stainless steel, or other materials. The bushings 150 can be reinforced with biocompatible metals or other biocompatible materials.

The bushings 153, 154 can be preassembled and connected to the clamp member 160. The clamp member 160 can then be positioned with respect to the platform member 152 and thereafter connected together with the set screw 170. The guiding connector 120 of FIGS. 5 and 6 permits the surgeon to slide the bushings 150 over the spinal rods and then position the rods and bushing members on the platform member 152 which may be integral with the bone connecting portion 130 of the guiding connector 120. The bushing 150 preferably is permitted to rotate along the X, Y, and Z axis plus translate or slide along the spinal rod.

Surgeons often bend spinal rods and create a desired rod shape in order to better fit the patient's spine or create the desired curvature for the patient's spinal column. The adjustability of the bushing 150 with respect to the guiding connector 120 provides increased flexibility. Once the desired orientation and position of the bushing 150 is set, the doctor can tighten the set screw 170 to position the bushing 150 in place on the platform member 152. The guiding connectors 120 can be used in the systems and constructs described in FIGS. 1 and 3, 4 to direct the growth of the spinal column 7 along a desired growth path.

Referring to FIGS. 7 and 8, a third preferred guiding connector 120' with moveable bushings 150' is illustrated. The guiding connector 120' of FIGS. 7 and 8 include a bone connecting portion 130' and a guiding portion 140'. The guiding portion 140' may include one or more sleeve connectors 175, one or more bushings 150' and a nut 185. The embodiment of FIGS. 7 and 8 illustrates using two sleeve connectors 175. Each sleeve connector 175 may include a sleeve 176 defining a bore 177 for receiving the bushing 150'. The sleeve connector 175 further includes a recess 178 for receipt of the bone connecting portion 130'. The sleeve connectors 175 are placed over the bone connecting portion 130' by placing the post 132 up through the recess 178. The sleeve connectors 175 are adjustable on the post 132 so that the bores 177 may be parallel or oriented at angles relative to one another. The nut 185 can lock the position of the sleeve connectors 175 on the bone connecting portion at desirable relative angles.

The bushing 150' can be configured and arranged similar to the bushings 150 and may have an exterior surface that preferably is frusto-spherically shaped and able to pivot, rotate and articulate with respect to the sleeve 176. The bushing 150' also preferably contains a bore 142' for receiving the spinal rods 10. The spinal rods 10 are configured to slide and glide with respect to the bushing 150' in-situ. After the angular orientation and position of the bushings 150' are adjusted, a surgeon can fix the position of the bushing 150' by tightening the nut 185 on the top of the shaft 137. The post 132 preferably has screw threads to mate with screw threads on the nut 185. After the nut 185 is tightened, the position and orientation of the sleeve connectors 177 and the bushings 150' is preferably fixed while still permitting the spinal rods 10 to slide and glide through the bushing 150'.

In an alternative embodiment, the sleeve connector 175 can be formed as a C-clamp having two legs extending there from which are compressed together in order to clamp the position of the bushing 150' with respect to the sleeve connector 175. When the nut 185 is tightened the first leg of the sleeve connector 175 is compressed into the second leg of the sleeve connector 175 making the bore 177 of the sleeve 176 smaller, thus clamping the position and orientation of the bushing 150' in the sleeve 176.

Referring to FIGS. 9A-9B, a fourth preferred embodiment of a guiding connector 120" for use in a spinal stabilization and guiding system is shown. The guiding connector 120" includes bone connecting portion 130", preferably in the form of a pedicle screw shaft 137" that is cannulated, and a guiding portion 140". The guiding portion 140" includes a housing member 165" having openings for one or more bushings 150". The bushings 150" may be shaped and configured the same as or similar to bushings 150, 150'. A cable 162 and crimp 164 connect the housing member 165" to the bone connecting portion 130".

The pedicle screw shaft 137" has a longitudinal bore (not shown) forming a cannulation that extends preferably from the tip of the screw along the longitudinal axis of the screw and extends into its distal end. Cable 162 extends through the cannulated screw along the longitudinal bore and extends beyond the distal end portion of the screw shaft 137". A channel 161 extends through the housing member 165" and is sized and configured to receive cable 162 there through. In use, bone connecting portion 236 may be anchored into the vertebrae or other bone with the cable 262 extending there from. The spinal rods may be inserted through the bushings 150" and the housing member 165 preferably slides down the cable 262 to the bone connecting portion 130". A crimp 164 may thereafter be inserted onto and slid along cable 162 and placed at the desired location along the cable 162 whereby the surgeon or other operator may secure the crimp 164 to the cable 162 by crushing it into position. Securing the crimp 164 to the cable preferably secures the housing member 165" to the cable 162 at the desired location and preferably fixes the housing member 165" with respect to the bone connecting portion 130". The spinal rods 10 are permitted to slide and glide through bushings 160" in guiding connector 120" thus enabling growth and lengthening of the spine along a path preferably defined by the spinal rods. The guiding connectors 120', 120" can be used in systems and constructs described and shown in FIGS. 1 and 3, 4 to direct the growth of the spine along a desired path.

Referring to FIGS. 10A-10C, a fifth preferred embodiment of the guiding connector 220 for use with a spinal stabilization and guiding system is shown and described. The guiding connector 220 includes bone connecting portion 230, preferably in the form of a pedicle screw shaft 237, and a guiding portion 240. The guiding portion 240 of FIGS. 10A and 10C includes a platform member 265, one or more bushings 250, cable member 262 and a stop member 267. In the embodiment of FIGS. 10A-10C, two bushings 252, 254 are utilized, although one bushing, or more than two bushings are contemplated. The bushings 252, 254 may be able to polyaxial rotate with respect to the platform member 265 and/or a bushing housing (not shown). The bushings 252, 254 alternatively may be fixed with respect to the platform member 265. The platform member 265 in the embodiments of FIGS. 10A and 10C contains the two bushings 252, 254, the stop member 267 and cable member 262. One end 263 of the cable member 262 is connected to the stop member 267 and cable 262 extends from the stop member 267. The platform member 265 includes a hub member 266 which includes a recess 267 for receiving the top end 233 of the bone connecting portion 230. The hub 266 preferably connects the platform member 265 to the bone connecting portion 230. The hub 266 has a transverse passageway 269 for receipt of the cable 262 there through.

The spinal rods 10, 10' are inserted through the bores 242, 244 located in the bushings 252, 254 and the cable 262 then may be wrapped around the exterior of the bushing 254, through the passageway 269 in the hub 266, around the bushing 252 and through a passage 268 formed in the stop member 267 so that the second end of the cable 262 extends out of the stop member 267. Alternatively or additionally, the cable 262 may extend through an opening 233 formed in the bone connecting portion 230 to connect the platform member 265 and bushings 250 to the bone connecting portion 230. The stop member 267 may incorporate a crimp mechanism or cable tie mechanism to fix and lock the position of the cable 262 with respect to the stop member 267. A user may be able to adjust the tension force in the cable 262 and thus adjust the tension on the guiding connector 220 and the compression force on the bushings 252, 254. Cable 262 is locked into position to retain the bushings 250 and spinal rods 10, 10' on the guiding connector 220, preferably in a manner to position the bushings 252, 254 in a desired direction and orientation to permit the spinal rod 10 to glide and slide through the guiding connector 220 to correct and/or define a growth path.

In an alternative embodiment, instead of stop member 267, a crimp 264 (not shown) may be applied to the end of the cable 262 and crushed and locked into position to retain the bushings 250 on the platform member 265 and the bone connecting portion 230. The embodiments of FIGS. 9 and 10 have been described in connection with the use of a cable 262 and optionally a crimp 264. It can be appreciated that a cable tie could be utilized and substituted for the cable and stop member and/or the cable and crimp.

Referring to FIG. 11 a sixth preferred embodiment of a guiding connector 220' is shown and described. The guiding connector 220' includes bone connecting portion 230', preferably in the form of a pedicle screw shaft 237', and a guiding portion 240'. The bone connecting portion 230' has an opening 233' formed in its top. The guiding portion 240' comprises the top portion of the bone connecting portion 230' configured to form a recess or bay 293' to receive spinal rod 10. Bay 293' is open at the top. Spinal rod 10 is position in the bay 293' and a cable tie 262' is inserted through the opening 233', wrapped around the spinal rod and tightened to secure the spinal rod to the bone connecting portion 230'. The bay 293' formed in the top portion of the bone connecting portion 230' is preferably formed as a bearing element and the cable tie 262' secures the rod but permits the rod to slide relative to the bay 293' (top surface of the rod connecting portion) and the cable tie 262'. Preferably the bay 293' and cable tie 262' are designed and treated to minimize friction and promote sliding of the spinal rod 10.

Referring to FIGS. 12A-12D, a seventh preferred embodiment of a guiding connector 320 for use in a guiding system for stabilizing the spine and providing a growth path is provided. Guiding connector 320 includes a bone connecting portion 330, preferably in the form of a pedicle screw shaft 337, and a guiding portion 340. Guiding portion 340 includes a platform member 365 having wings 380 and 385, central protrusion 390 and a connecting portion 395. The connecting portion 395 connects the platform 365 to the bone connecting portion 330. The connecting portion 395 has flexible fingers 396 that preferably snap into the opening 333 in the bone connection portion 330. The wings 380, 385 have an inner surface and an exterior surface and preferably are flexible and bendable and may be used to attach one or more rods 10 to the guiding connector 330. The platform portion 365 (preferably the protrusion and wings) and is preferably made of plastic or other polymer material, preferably PEEK or ultra high molecular weight polyethylene (UHMWPE), to facilitate sliding and movement of the spinal rods through the wings 380, 385. The central protrusion 390 is optional and preferably separates the two spinal rods and preferably provides a bearing surface to facilitate relative sliding of the rods within the platform member 365. The wings 380, 385, and/or the platform member 365 may further be composed of metal or metal alloy or other materials to strengthen and reinforce the platform member 365. The bearing surfaces may further be polished or coated with materials to promote sliding movement of the rods within and through the folded wings 380, 385.

In use, the rods 10 are inserted through the top opening 361 so that they rest in the recess or bays 393 formed between the central protrusion 390 and the wings 380, 385. After the rods 10 are placed in the platform member 365 one of the wings 380, 385 is bent and flexed around the spinal rods. Next the other wing 380, 385 is bent around the spinal rods 10 and the first wing 380, 385. A cable tie 362 is thereafter inserted through the bore 333 and extends around the exterior surface of the folded wings 380, 385 and tightened to secure the position of the rods 10 relative to the guiding connector 330 so as to permit sliding motion of the spinal rods 10 relative to the guiding connector 330. Movement of the guiding connector 320 along the spinal rod constrains the motion and growth of the vertebrae preferably along a predetermined path. To strengthen and facilitate the bending nature of the wings 380, 385, the wings may have ridges 398 formed along the width of the wings 380, 385. Cable tie 362 also facilitates securing the platform member 365 to the bone connecting portion 330.

While the guiding connector 320 has been shown and described as having two (2) wings 380, 385 and one central protrusion 390 forming two (2) recess or bays 393 for two (2) spinal rods 10, 10', it can be appreciated that the platform member may include only one wing, no protrusions 390, and only one recess 393 for one spinal rod. The platform member may also be configured for more than two spinal rods, and may include two or more protrusions 390, two or more recesses 393 and more than two wings.

Referring to FIGS. 13A-C, an eighth preferred embodiment of a guiding connector 420 is shown and illustrated for use in a system for stabilizing the spine and restricting and/or facilitating growth of the spinal column 7 along a predetermined path. The guiding connector 420 includes a bone connecting portion 430 preferably in the form of a screw 437 having threads for anchoring in vertebral bone. Guiding connector 420 further includes a guiding portion 440 attached to the bone connecting portion 430. Guiding portion 440 includes platform member 465, one or more wings 480, 485, and a central protrusion 490. The guiding connector 420 is similar to the connector 320 described above. The platform member 465 is connected to the bone connecting portion 430 in a manner that preferably provides a passageway 433 for receipt of cable tie 462 as shown and described below.

Connecting mechanism 495 includes two support members 496, 496' extending from the bone connecting portion 430. Support members 496, 496' have bores 497, while central protrusion 490 of the platform member 465 has a cavity 453 (not shown). A pin rivet or screw 499 is received through bores 497 and cavity 453 to connect wings 480, 486 to the connecting portion 495. The pin 499 in the bores 497 and the cavity 453 preferably permits the platform member 465 to rotate, swivel or pivot with respect to the bone connecting portion 430. The bendable, flexible wings 480, 485 may extend as shown in FIG. 13A, or alternatively could be curved to form recesses or bays 493, 494 for the spinal rods 10. The guiding portion 440 may also include only one wing 480, and one central protrusion 490 as shown in FIG. 13B. Additional wings, protrusions and optional recesses 493 may be provided in guiding portion 440.

In use, the spinal rods 10 are top loaded into the opening 461 with each spinal rod 10 inserted on one side of the guiding connector 420 so that each spinal rod 10 is located between the protrusion 490 and a wing 480, 485. When the rods 10 are adjusted into their desired position, the cable tie 462 is inserted through passageway 433 and wrapped around the wings 480, 485 and tightened to secure the spinal rods 10 to the guiding connector 420. FIG. 13C illustrates cable tie 462 passed through the passageway 433. The embodiments illustrated in FIGS. 13A and C can accommodate two spinal rods, while the embodiment illustrated in FIG. 13B is designed to hold a single spinal rod. FIG. 13D illustrates a system utilizing guiding connector 420' implanted into a schematically represented spinal column. The platform member 465 preferably forms a bearing member with the protrusion 490 and the wings 480, 485, preferably formed to facilitate and promote relative sliding of the spinal rods 10.

The guiding connector 320, 420, 420' and cable tie 462 may be implanted using an implant holder 425 as illustrated in FIG. 14. Implant holder 425 includes a handle portion 426, a distal holder 427 and a proximal holder 428. The proximal holder 428 has a channel 422 and is inserted over the distal end 421 of the implant holder 425. The shaft portion 423 of the implant holder 425 is inserted through the channel 422 and the proximal holder 428 is slid up the shaft 423 of the handle portion 426 so that it is loaded and preferably contacting or proximate to the stop member 429. The distal holder 427 has a channel 424 and the distal end 421 of the handle portion 426 is inserted through the channel 424 and the distal holder 427 is slid up the shaft portion 423 of the handle portion 426 so that it is proximate the proximal holder 428 previously loaded on the handle portion 426. The implant holder 425 with the proximal and distal holders 427, 428 proximate the stop member 429 is in the ready position to receive and connect to the guiding connector 420 and cable tie 462.

To load the guiding connector 420, 420' and cable tie 462 on the implant holder 425, the distal end 421 of the shaft 423 of the handle portion 426 is positioned proximate to the central protrusion 490, 490' of the guiding connector 420, 420'. The cable tie 462 is inserted through the passageway 433 prior to or after the guiding connector 420, 420' is positioned proximate the implant holder 425. The wings 480, 485 and cable tie 462 preferably are bent and deflected upward to a position along the sides of the shaft portion 423. The distal holder 427 is thereafter slid down the shaft portion 423 toward the distal end 421 of the handle portion 426. The ends of the cable tie 262 are inserted through the channel 424 of the distal holder 427 and the distal holder 427 is slid further down the shaft 423 until the wings 480, 485 are also contained within the channel 424. The distal holder 427 may cooperate with a notch or other retaining mechanism to retain the distal holder 427 on the proximal end 421 of the handle portion 426 retaining the cable tie 462 and wings 480, 485 to the implant holder 425.

The optional proximal holder 428 is then slid down the shaft 423 toward the distal end 421 of the handle portion 426 and the ends of the cable tie 462 are inserted through the channel 422 of the proximal holder 427 to retain the cable tie ends to the handle portion 426. The cable tie 462 and guiding connector 420 in this manner is loaded onto and retained on the implant holder 425 as shown in FIG. 14 and ready for insertion into the instrument for connecting the guiding connector 420 to the desired bone. The guiding connector 420, 420', cable tie 462 and implant holder 425 may be preassembled, packaged, sterilized and sold as a unit, or the component parts can be supplied separately and assembled prior to or during the surgical procedure.

The steps of inserting the guiding connector, cable tie and implant holder 425 into a driver instrument is illustrated in FIGS. 16A-16C. The driver facilitates providing torque to the guiding connector 420 to attach it to a vertebra. The driver 434 is preferably configured as a hollow sleeve 439 having a central cannulation and a torque transmitting interface at its distal end. The torque transmitting interface is designed to interface and cooperate with a mechanism or structure on the guiding connector to transmit torque to the guiding connector.

The implant holder 425 with preassembled connector 420, 420' and cable tie 462 as illustrated in FIG. 14 is inserted into the proximal end of the driver 434 and down the hollow sleeve 439 as shown in FIG. 16A until the distal holder 427 contacts and abuts against the proximal end of the sleeve 439. The implant holder 425 with guiding connector 420 and cable tie 462 is further inserted down the sleeve 439 so that the distal holder 427 slides proximally toward the proximal holder 428 and stop member 429 as shown in FIG. 16B. The implant holder 425, and shaft 423, continue traveling down the sleeve 439 (with distal and proximal holders 427, 428 sliding toward the stop member 429) until the guiding connector 320, 420, 420' extends out of the distal opening of the sleeve 439 as shown in FIG. 16C. The implant holder 425 may extend into sleeve 439 until the stop member 429, proximal holder 427 and distal holder 428 contact and abut each other as shown in FIG. 16C. Thus a smooth push on the implant holder 425 causes the holder 425 to slide easily into the driver 434 whereby the distal and proximal holder 427, 428 slide back automatically.

Referring to FIGS. 17-19, a ninth preferred embodiment of a guiding connector 520 is shown and illustrated for use in a system for guiding and stabilizing the growth of the spinal column 7 along a predetermined path. The guiding connector 520 includes a bone connecting portion 530, preferably in the form of a lamina clamp for attaching to the lamina of a vertebrae. The bone connecting portion 530 includes front legs 531, 531' and back legs 534, 534' that are preferably adjustable by adjusting mechanism 532, which may include a screw element 533. Rotation of screw element 533 preferably adjusts the separation of front leg 531 from front leg 531', and adjusts the relative separation of back leg 534 from back leg 534'. Screw element 533 preferably also adjusts the relative separation of the front legs 531, 531' from the back legs 534, 534'.

Guiding connector 520 further includes a guiding portion 540 which includes an integral lateral rod-connecting member 545. Bone connecting portion 530 may have one or more sleeve elements 537 to receive one or more lateral rod connecting members 545. Lateral rod connecting members 545 are preferably laterally adjustable and securable to sleeve elements 537. A set screw (not shown) may permit adjustment and locking of the lateral rod connecting member 545 relative to the sleeve element 537. The lateral rod connecting member 545 adjusts the distance the spinal rods may be positioned relative to the spinal column and may be used to pull the spinal rods closer to the bone connecting portion or push the bone connecting portion further away.

The lateral rod connecting member 545 as shown in FIG. 19 may include a housing 565 which may contain one or more bushing elements 550. The bushings 550 preferably have a frusto-spherical outer surface and preferably can polyaxially rotate in housing 565. Alternatively, the bushings 550 may be fixed relative to housing 565. The bushing 550 contains a bore 542 through which spinal rods 10 may be received. The spinal rods 10, 10' preferably can move with respect to the bushing 550 when implanted within a patient.

Referring to FIG. 20, a tenth embodiment of a guiding connector 620 is shown. Guiding connector 620 includes the guiding portion 640 of the embodiment of FIGS. 17 and 19 (including the lateral rod connecting member 545). Bone connecting portion 630 includes two (2) side loading pedicle screws 15' (which may be monoaxial, monorotational, or polyaxial) arranged to receive lateral connecting portion 645 so that lateral rod connecting portion 645 extends transverse to the axis of the spinal column 7.

Lateral rod connecting offset connectors such as those illustrated in FIGS. 17-20 may be particularly useful where there is a severe curvature of the spine, such as, for example, where the implanted spinal rods are unable to extend along the vertebrae of the spinal column.

Referring to FIGS. 21 and 22 an eleventh embodiment of a guiding connector is shown which includes a lateral offset connector. Guiding connector 720 includes a bone connecting portion 730, which in the embodiments of FIGS. 21 and 22 preferably is a screw 737, and a guiding portion 740. Guiding portion 740 includes a lateral connector 765 which has two rod receiving bores 742 which are configured to receive spinal rods 10, 10' and permit, facilitate and promote movement of rods 10, 10' relative to lateral connector 765. The lateral connector 765 has a further port 763 for receiving a connector 775 for attaching the lateral connector 765 to the bone connecting portion 730. In the embodiment of FIGS. 21 and 22 the connector 775 preferably is a cable tie 762. The connector 775 preferably is relatively stiff to provide support to rods 10, 10'.

The port 763 is preferably configured to accept the connector 775 from a proximal or distal side so that lateral connector 765 can be attached to bone connecting portion 730 in both configurations shown in FIGS. 21 and 22. In the construct of FIG. 21, the port 763 is arranged to be closest to the bone connecting portion 730 such that the connector 775 does not extend or wrap around the spinal rods 10, whereas in FIG. 22 the port 763 is arranged in the construct to be distal to the bone connecting portion 730 such that the connector 775 extends and wraps substantially around the lateral connector 765 and spinal rods 10, 10' which may provide more support to the spinal rods 10, 10'. The tension in the cable tie 762 can be adjusted by the user and can be used to pull the spinal rods closer to the bone connecting portion 730 preferably to help straighten the spinal column.

Referring to FIG. 23 an twelfth embodiment of a guiding connector in the form of a parallel connector is shown. The guiding connector 820 has a guiding portion 840 but no bone connecting portion. The guiding portion 840 has a housing 865 that includes a hook portion 867 that preferably is fixedly secured to spinal rod 10 with a set screw. The set screw is optional and may be eliminated such that spinal rod 10 may move relative to housing 865. The housing 865 also includes a bushing 850, preferably a bushing 850 that can polyaxial rotate relative to the housing 865. The bushing 850 has a bore 842 to receive spinal rod 10' there through. Spinal rod 10' preferably can translate and slide through bushing 850 in a direction relatively parallel to the axis of spinal rod 10.

Referring to FIG. 24, a thirteenth embodiment of a guiding connector in the form of an alternative parallel connector is shown. The guiding connector 920 has a guiding portion 940 but no bone connecting portion. The guiding portion 940 has a housing 965 that preferably has one or more bores 942 preferably configured as bearing elements to receive spinal rods 10, 10'. In the parallel connector 920 the housing has two bores 942 to receive spinal rods 10, 10'. Preferably the spinal rods 10, 10' can translate and slide through bores 942. One or more set screws (not shown) may be provided to lock the position of either spinal rod 10, 10'. One or more openings 961 which extend into the bores 942 may be provided to permit side loading of the spinal rods 10, 10'. The openings 961 are preferably smaller than the diameter of the spinal rods so that the spinal rods can be snapped into the bores 942 and be retained in the housing 965. A channel 983 may be formed substantially around the side of the parallel connector 920 to receive a securing strap, such as, for example a cable tie. The securing strap 962 may secure spinal rods 10, 10' in bores 942 while permitting the rods to translate and slide in situ when the system is implanted in a patient. The parallel connectors preferably promote keeping the spinal rods parallel and from contacting each other to promote and encourage ease of sliding and the telescopic action.

As will be appreciated by those of skill in the art, any or all of the components described herein may be provided in sets or kits so that the surgeon may select various combinations of components to perform a stability procedure and create a system which is configured specifically for the particular needs and anatomy of a patient. It should be noted that one or more of each component may be provided in a kit or set. In some kits and sets, the same device may be provided in multiple quantities, and in different shapes and/or sizes.

The stabilization and guiding system is preferably provided to the user in a kit that may include (1) one or more elongated support members such as, for example, spinal rods; (2) one or more bone anchors for fixed securing the elongated support members to a bone (for example, a vertebrae) preferably to form one or more anchor points; (3) one or more guiding connectors with bone connecting portions and mechanisms; (4) one or more lateral connectors; and (5) one or more parallel connectors.

The guiding connectors may be preassembled and include one or more securing elements such as cable ties, straps or cables. The guiding connectors may be preassembled and loaded onto or into an implant holder and/or a driving instrument. The guiding connectors and spinal rods may be made from any biocompatible material now known or hereafter discovered including, but not limited to, metals, such as, for example, titanium, titanium alloy, stainless steel, cobalt chromium, Nitinol, etc. Other materials, such as, for example, plastics, polymers, composites, ceramics and any other material now know or later discovered also may be used for the guiding connectors and spinal rods. The rods and the guiding connectors, or portions thereof can be polished and or coated with material to facilitate and promote the relative motion of the spinal rods relative to the guiding connectors.

While the foregoing description and drawings represent the preferred embodiments of the present invention, it will be understood that various additions, modifications, combinations and/or substitutions may be made therein without departing from the broad spirit and scope of the present invention as defined in the accompanying claims. In particular, it will be clear to those skilled in the art that the present invention is not limited to the particular embodiments shown and described but may be embodied in other specific forms, structures, arrangements, proportions, and with other elements, materials, features and components, without departing from the spirit or essential characteristics of the invention. One skilled in the art will appreciate that the invention may be used with many modifications of structure, arrangement, proportions, materials, features, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, with the scope of the invention being indicated by the appended claims and not limited to the foregoing description.

The invention claimed is:

1. A system to stabilize and guide the growth of a spinal column having a first vertebra and a second vertebra, the system comprising:
   a cable;
   an elongated support member that extends along a longitudinal direction and has an outer surface;
   at least one guiding connector having a bone connecting portion and a guiding portion, the bone connecting portion configured and adapted to firmly secure the guiding connector to the first vertebra and the guiding portion having a bearing element defining a first passageway having an inner surface and a second passageway having an inner surface, the second passageway being substantially parallel to the first passageway, each of the first and second passageways being configured to selectively and individually slidably receive a first portion of the elongated support member, the guiding portion further including a transverse opening located between the first passageway and the bone connecting portion, the transverse opening configured to receive the cable, the cable being configured to secure the inner surface of the first passageway to the outer surface of the first portion of the elongated support member, wherein the bearing element permits relative sliding movement of the elongated support element in the first passageway; and
   at least one bone fixation element having an elongated support member receiving channel configured to receive a second portion of the elongate support member, the second portion spaced from the first portion along the longitudinal direction, a locking mechanism and a bone anchoring portion, the bone anchoring portion configured and adapted to firmly secure the bone fixation element to the second vertebra to provide a firm anchoring point, and the locking mechanism configured and adapted to firmly secure the second portion of the elongated support member in the channel,
   wherein the guiding connector is configured to be moveable along the elongated support member when 1) the at least one guiding connector is anchored to the first vertebra, 2) the at least one bone fixation element is anchored to the second vertebra, and 3) the elongated support member is firmly secured in the channel.

2. The system of claim 1, wherein the bone connecting portion of the at least one guiding connector comprises at least one of the group of hooks, pins, tacks, stakes, nails, blades, screws and clamps.

3. The system of claim 1, wherein the bearing element has a front face, a back face, sides, a plurality of passageways extending through the bearing element from the front face to the back face, and a housing surrounding the sides of the bearing element and connecting the bearing element to the bone connecting portion, wherein an interior surface of the bearing element defines the passageways, and is formed of a polymer material.

4. The system of claim 1, wherein the guiding connector comprises a platform member, at least one bushing, a clamp member and a securing mechanism, wherein the bushing has at least one passageway and has an outer side surface, the platform member and clamp member surround at least a portion of the side surface of the bushing, and the securing mechanism has an unlocked position that permits the bushing to rotate polyaxially with respect to the platform member and the clamp member and a locked position which fixes the position of the bushing with respect to the platform member and the clamp member.

5. The system of claim 1, wherein the guiding portion further comprises:
   a platform member and at least one bushing, the bushing mounted on the platform member, and
   wherein the cable comprises first and second ends and extends at least partially around the bushing and secures the bushing on the platform member and to the bone connecting portion.

6. The system of claim 5 wherein the guiding portion further comprises a stop member wherein the cable extends out of the stop member and wraps around at least a portion of the bushing and the cable is adjustably fixedly securable to the stop member to adjust the tension in the cable.

7. The system of claim 1, wherein the guiding portion comprises a platform member that has at least one flexible wing, the guiding portion further having a connecting portion that attaches the platform member to the bone connecting portion, and the at least one wing is bendable to form at least a portion of the bearing element.

8. The system of claim 7, wherein the at least one flexible wing includes an inner surface and an outer surface, wherein the cable is configured to extend around the outer surface of the at least one wing and through the transverse opening to secure the elongated support member in the bearing element formed by the at least one wing.

9. The system of claim 7, wherein the at least one flexible wing includes an inner surface and an outer surface, and the connecting portion pivotally attaches the platform member to the bone connecting portion, wherein the cable extends around the outer surface of the at least one wing to secure the elongated support member in the bearing element formable by the at least one wing.

10. The system of claim 9, wherein the platform member further comprises a protrusion member and at least two flexible wings wherein the protrusion member and wings form at least a portion of the bearing element for the receipt of at least two elongated support members.

11. The system of claim 1, wherein the guiding connector is configured to be moveable along the elongated support member to permit and control the growth of the spinal column along a predetermined path, and the predetermined path is defined by the elongated support member.

12. A system to stabilize and guide the growth of a spinal column having a first vertebra and a second vertebra, the system comprising:
   a flexible cable having first and second ends;
   an elongated support member; and a guiding connector configured to slidably receive the elongated support member, the guiding connector further comprising a bone connecting portion having a threaded shaft for anchoring the guiding connector to the first vertebra and a guiding portion;

wherein the guiding portion further comprises
- a platform member; and
- a first flexible wing physically connected to a first side portion of the platform member and a second flexible wing physically connected to a second side portion of the platform member, the second side portion being opposite the first side portion, the first and second flexible wings each having an end, an inner surface, and an outer surface;

a connecting portion that attaches the platform member to the bone connecting portion, the connecting portion defining in part a transverse axial passageway located between the connecting portion and the platform member and designed and configured to accept the flexible cable;

wherein when the flexible cable is positioned within the transverse axial passageway the flexible cable is adjacent the outer surface of both the first and second flexible wings and extends parallel to the first and second wings and the cable is flexible such that the cable can be tightened and bend the first and second flexible wings from an extended configuration where the first and second flexible wings extend outwardly away from the platform member to a curved configuration where the first flexible wing, in conjunction with the platform member, forms a first passageway defined in part by the inner surface of the first flexible wing and where the second flexible wing, in conjunction with the platform member, forms a second passageway defined in part by the inner surface of the second flexible wing;

wherein the first and second passageways are configured to receive and slide along the elongated support member.

13. The system of claim 12 wherein the first passageway defines a first central axis of insertion and the second passageway defines a second central axis of insertion, such that the first central axis of insertion is substantially parallel to the second central axis of insertion, and such that the first central axis of insertion is substantially perpendicular to the threaded shaft of the bone connecting portion.

* * * * *